US008450284B2

(12) United States Patent
Boato et al.

(10) Patent No.: US 8,450,284 B2
(45) Date of Patent: May 28, 2013

(54) COILED-COIL LIPOPEPTIDE HELICAL BUNDLES AND SYNTHETIC VIRUS-LIKE PARTICLES

(75) Inventors: Francesca Boato, Tegna (CH); Anabelle Freund, Aarau (CH); Arin Ghasparian, Zürich (CH); Kerstin Möhle, Wettswil (CH); John A. Robinson, Wermatswil (CH); Richard M. Thomas, Kew (GB)

(73) Assignee: Universitaet Zuerich, Zurich (CH)

( * ) Notice: Subject to any disclaimer, the term of this patent is extended or adjusted under 35 U.S.C. 154(b) by 664 days.

(21) Appl. No.: 12/518,269

(22) PCT Filed: Dec. 6, 2007

(86) PCT No.: PCT/EP2007/010601
§ 371 (c)(1),
(2), (4) Date: Sep. 22, 2009

(87) PCT Pub. No.: WO2008/068017
PCT Pub. Date: Jun. 12, 2008

(65) Prior Publication Data
US 2010/0015173 A1    Jan. 21, 2010

(30) Foreign Application Priority Data
Dec. 9, 2006    (EP) .................................. 06025497

(51) Int. Cl.
*A61K 38/16*    (2006.01)
*A61K 38/00*    (2006.01)

(52) U.S. Cl.
USPC ............................ 514/21.3; 530/324; 514/3.2

(58) Field of Classification Search
None
See application file for complete search history.

(56) References Cited

FOREIGN PATENT DOCUMENTS
WO    98/07752 A1    2/1998
WO    WO-98/07752    *    2/1998

OTHER PUBLICATIONS

Woolfson, 2005, Advances in Protein Chemistry, Academic Press, NewYork, NY, US, vol. 70, pp. 79-112.*
Winger, 1996, Biomaterials, 17, 437-441.*
Berndt P. et al: "Synthetic Lipidation of Peptides and Amino Acids: Monolayer Structure and Properties" in Journal of the American Chemical Society, American Chemical Society, Washington, DC, US, vol. 117, No. 37, Sep. 20, 1995, pp. 9515-9522.
Winger T. M. et al: "Lipopeptide conjugates: biomolecular building blocks for receptor activating membrane mimetic structures" in Biomaterials, Elsevier Science Publishers BV., Barking, GB, vol. 17, No. 4, 1996, pp. 437-441.
Eisele Frank et al: "Synthesis and membrane binding properties of a lipopeptide fragment from influenza virus a hemagglutinin." in Chemistry (Weinheim an der Bergstrasse, Germany), vol. 8, No. 15, Aug. 2, 2002, pp. 3362-3376.

(Continued)

*Primary Examiner* — Satyanarayana R Gudibande
(74) *Attorney, Agent, or Firm* — Joyce von Natzmer; Agris & von Natzmer LLP

(57) ABSTRACT

The invention relates to lipopeptide building blocks consisting of a peptide chain comprising a coiled-coil domain, linked covalently to a lipid moiety comprising long alkyl or alkenyl chains, and optionally linked to an antigen; and to helical lipopeptide bundles and synthetic virus-like particles formed by aggregation. The nanometer size and shape of these bundles and particles, their stability under aqueous physiological conditions, their chemical composition, the possibility to incorporate B- and T-cell epitopes, and their production by chemical synthesis, make them highly suitable as vaccine delivery vehicles.

20 Claims, 10 Drawing Sheets

OTHER PUBLICATIONS

Woolfson D. N: "The Design of Coiled-Coil Structures and Assemblies" in Advances in Protein Chemistry, Academic Press, New York, NY, US, vol. 70, 2005, pp. 79-112.

Perera Rushika et al: "A heterologous coiled coil can Substitute for helix I of the Sindbis virus capsid protein." in Journal of Virology Aug. 2003, vol. 77, No. 15, pp. 8345-8353.

Zhu Jieqing et al: "The fusion protein core of measles virus forms stable coiled-coil trimer." in Biochemical and Biophysical Research Communications Dec. 20, 2002, vol. 299, No. 5, pp. 897-902.

Pelletier A. et al: "Self-Association of Herpes Simplex Virus Type1 ICP35 is Via Coiled-Coil Interactions and Promotes Stable Interaction With the Major Capsid Protein" in Journal of Virology, The American Society for Microbiology, US, vol. 71, No. 7, Jul. 1997, pp. 5197-5208.

Liu Jie et al: "A seven-helix coiled coli." in Proceedings of the National Academy of Sciences of the United States of America, vol. 103, No. 42, Oct. 17, 2006, pp. 15457-15462.

Boato Francesca et al: "Synthetic virus-like particles from self-assembling coiled-coil lipopeptides and their use in antigen display to the immune system." in Angewandte Chemie (International Ed. in English) 2007, vol. 46, No. 47, pp. 9015-9018.

Epand R. M.: "Biophysical Studies of Lipopeptide-Membrane Interactions" in Biopolymers, New York, NY, US, vol. 43, No. 1, 1997, pp. 15-24.

Zinkernagel: "Immunology Taught by Viruses" in Science, vol. 271, Jan. 12, 1996, pp. 173-178.

* cited by examiner

COILED-COIL LIPOPEPTIDE HELICAL BUNDLES AND SYNTHETIC VIRUS-LIKE PARTICLES

This is the U.S. national stage of International application PCT/EP2007/010601, filed Dec. 6, 2007 designating the United States, which claims priority from European Application EP 06025497.6, filed Dec. 9, 2006.

FIELD OF THE INVENTION

The invention relates to lipopeptide building blocks comprising a coiled-coil domain and optionally an antigen, which aggregate to helical lipopeptide bundles and synthetic virus-like particles. Synthetic virus-like particles carrying antigens are useful as vaccines.

BACKGROUND OF THE INVENTION

It is well known that isolated small peptides and proteins are usually only poorly immunogenic. Toxic adjuvants, like the well-known Freunds' complete adjuvant, are widely used to stimulate immune responses against subunit vaccines in animals, but many cannot be used in humans because of their toxic side-effects. The ideal situation would be to avoid completely the use of external adjuvants, but this typically results in poor immune responses. However, the (human) immune system generates robust immune responses against pathogens displaying repeated antigenic structures across a surface, e.g. that of a virus [Zinkernagel, R., Science, (1996), 171, 173-178].

Liposomes have received a great deal of attention over the past 30 years as carriers for pharmaceutical products, including drugs, nucleic acids, and biopharmaceuticals, and applications of liposomes as delivery vehicles for antigens, nucleic acids and drugs are well known. The properties of liposomes can be altered by coupling peptides or proteins to their surface in order to target specific receptors; creating systems known as proteoliposomes. Peptides and proteins have also been incorporated into liposomes for the purpose of generating immune responses [Leserman, L., J Liposome Res, (2004), 14, 175-189; Frisch, B., et al., Methods Enzymol., (2003), 373, 51-73]. The conjugation of peptides to lipids facilitates their insertion into liposomes, with the lipid anchored in the bilayer membrane, thus allowing recognition of the peptide by antibodies at the surface of the liposome. One of the drawbacks of liposomes as a general delivery vehicle is their instability in vivo, due to fast elimination from the blood and capture by the cells of the reticuloendothelial system [Torchilin, V. P., Nat. Rev. Drug Discov., (2005), 4, 145-160].

The potential advantages of using virus-like particles, composed of natural or genetically modified viruses and chimeras, including phages, or natural or genetically modified viral components, such as capsid proteins, surface proteins and glycoproteins, or fragments of these, in vaccine design have been recognized for some time [Felnerova, D., et al., Curr Opin Biotechnol, (2004), 15, 518-529; Garcea, R. L., et al., Curr Opin Biotechnol, (2004), 15, 513-517; Doan, L. X., et al., Rev Med Virol, (2005), 15, 75-88]. The production of such virus-like particles makes use of the natural viral processes of self-assembly. The natural self-assembling core structures of many viruses can be exploited using recombinant DNA technology to display one or more antigens on the surface of these particles. These virus-like particles are not accessible by chemical synthesis due to their large size and structural complexity. Patent applications WO 98/014564 and WO 00/035479 refer to "synthetic virus-like particles", although the particles referred to therein are based on natural or genetically modified virus particles, or components thereof, made using recombinant DNA and cell-based methods, not materials produced by chemical synthesis. WO 00/32227 describes the use of core particles of natural or non-natural origin to which antigens are attached in an ordered and repetitive fashion, exemplified by the use of recombinant Sinbis virus.

Considerable efforts have also been made to design self-assembling peptides and proteins for nanotechnological applications. Nanoscale morphologies have been produced based on designed amphiphilic peptides [Löwik, D. W. P. M., et al., Chem. Soc. Rev., (2004), 33, 234-245], including those having β-strand, β-sheet and α-helical secondary structures [Rajagopal, K., et al., Curr. Opin. Struct. Biol., (2004), 14, 480-486; Tu, R. S., et al., Adv. Drug Deliv. Revs., (2004), 56, 1537-1563]. Further examples of the use of lipopeptides to prepare nanostructured composite materials are found in the work of Stupp and co-workers [Behanna, H. A., et al., J. Am. Chem. Soc., (2005), 127, 1193-1200]. A peptide amphiphile was shown earlier to self-assemble into nano-fibres [Hartgerink, J. D., et al., Science, (2001), 294, 1684-1688].

One of the main problems in designing effective vaccines based on synthetic antigens has been their poor immunogenicity. Relatively small synthetic molecules tend to be poorly immunogenic. One approach to overcome this poor immunogenicity is to covalently conjugate the synthetic antigen to a carrier, such as a protein like tetanus toxin or keyhole limpet hemocyanin (KLH) [Herrington, D. A., et al., Nature, (1987), 328, 257-259]. The conjugate, however, must still be administered to an animal together with an adjuvant (e.g. alum or Freunds' adjuvant) in order to elicit a strong immune response. A number of other methods have been described for producing multi-epitope constructs incorporating B-cell and T-cell epitopes (reviewed in [Jackson, D. C., et al., Vaccine, (1999), 18, 355-361]).

Synthetic bacterial lipopeptide analogs have received wide attention in vaccine research, both for their adjuvant effects and as carriers for peptide antigens [Ghielmetti, M., et al., Immunobiology, (2005), 210, 211-215]. Lipids and lipopeptides are known to be capable of adjuvanting otherwise weak peptide immunogens [Jung, G., et al., Angew. Chem. Int. Ed., (1985), 10, 872; Martinon, F., et al., J. Immunol., (1992), 149, 3416]. Many lipopeptide constructs have been reported, in which a lipid with known adjuvant effects has been coupled to a peptide to generate self-adjuvanting vaccine candidates. Particularly well studied are tripalmitoyl-S-glyceryl cysteine (N-palmitoyl-S-(2,3-bis-(O-palmitoyloxy)-propyl)-cysteinyl- or Pam3Cys) and dipalmitoyl-S-glyceryl cysteine (2,3-bis-(O-palmitoyloxy)-propyl)-cysteinyl- or Pam2Cys) [Ghielmetti, M., et al., Immunobiology, (2005), 210, 211-215]. These lipid moieties are found in lipoprotein components of the inner and outer membranes of gram-negative bacteria. Synthetic lipopeptides carrying these or related di-acylated or tri-acylated S-glyceryl cysteine residues at the N-terminus have been shown to be specific ligands of Toll-like receptors [Reutter, F., et al., J. Pept. Res., (2005), 65, 375-383; Buwitt-Beckmann, U., et al., Eur. J. Immunol., (2005), 35, 1-8]. Moreover, the conjugation of peptide antigens to Pam3Cys or Pam2Cys has been applied in the design of self-adjuvanting synthetic vaccine candidates (Bessler, W. G., et al., Int. J. Immunopharmac., (1998), 19, 547-550; Loleit, M., et al., Biol. Chem. Hoppe-Seyler, (1990), 371, 967-975; Muller, C. P., et al., Clin. Exp. Immunol., (1989), 78, 499-504]. Patent application WO 98/07752 describes the use for drug targeting purposes of lipopeptides, wherein the peptide portion may be a collagen-like sequence capable of inducing triple helical structures.

A number of reviews on coiled-coil design have appeared recently [Woolfson, D. N., Adv. Prot. Chem., (2005), 70, 79-112], including a volume of Advances in Protein Chemistry devoted to coiled-coils, collagen and elastomers [Parry, D. A. D., et al., Advancs in Protein Chemistry, (2005), 70]. Many natural viruses and microbes contain coiled-coil peptide sequences within their own surface proteins (e.g. hemagglutinin of influenza virus, or gp41 of human immunodeficiency virus-1 (HIV-1), or the F-glycoprotein of respiratory syncytial virus (RSV)).

SUMMARY OF THE INVENTION

The invention relates to lipopeptide building blocks (LBB) consisting of a peptide chain (PC) comprising a coiled-coil domain, linked covalently to a lipid moiety (LM) comprising two or three long hydrocarbyl chains, and optionally linked to an antigen (A); helical lipopeptide bundles (HLB) comprising two, three, four or five lipopeptide building blocks (LBB), the number of building blocks being determined by the properties of the coiled-coil domain in the peptide chain of the lipopeptide building blocks (LBB); and synthetic virus-like particles (SVLP) comprising a large number of helical lipopeptide bundles (HLB) and having a spherical or spheroidal structure with a lipid core and a peptidic outer surface.

The invention further relates to processes of production of lipopeptide building blocks (LBB), helical lipopeptide bundles (HLB) and synthetic virus-like particles (SVLP); to the use of lipopeptide building blocks (LBB), helical lipopeptide bundles (HLB) and synthetic virus-like particles (SVLP) carrying antigens in the preparation of vaccines; and to methods of vaccination using such vaccines. The invention likewise relates to pharmaceutical preparations containing synthetic virus-like particles carrying antigens.

The various compositions of the invention are useful for inducing immune responses for the prevention or treatment of diseases, disorders or conditions, including infectious diseases, allergies, cancer, drug addiction, poisoning, and generally to efficiently induce antigen specific immune responses.

PC, peptide chain comprising a coiled-coil domain; LM, lipid moiety; A, antigen; LBB, lipopeptide building block; HLB, helical lipopeptide bundle (a trimer is shown); SVLP, synthetic virus-like particle (with antigens).

Figure 2:
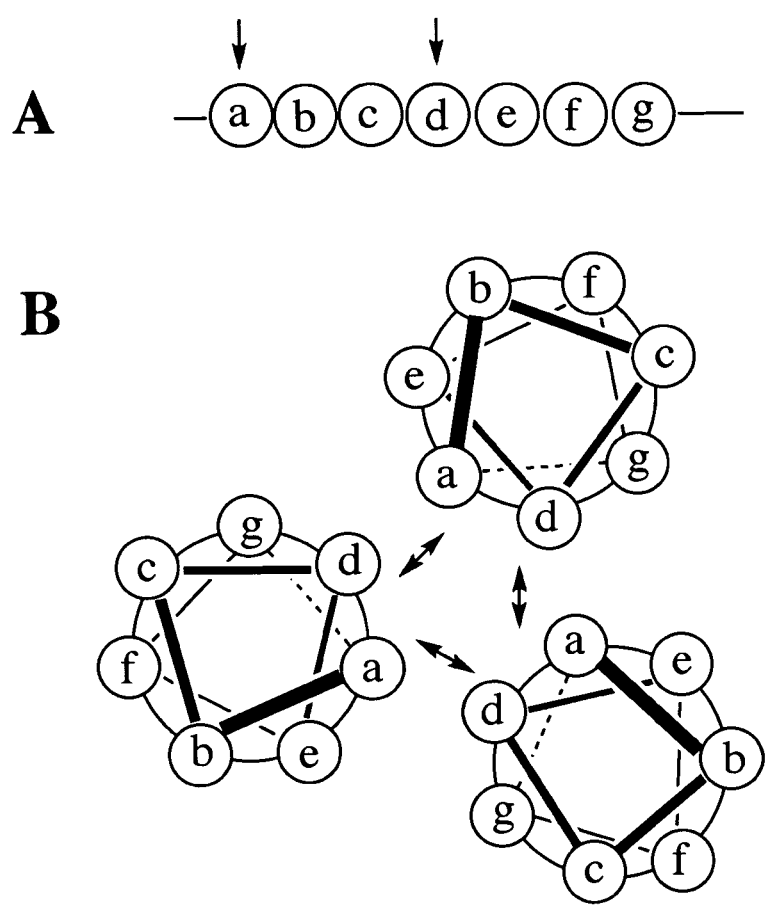

FIG. 2: Schematic representation of heptad motifs present in coiled-coil peptides A: Heptad. a, b, c, d, e, f, g: α-amino acid residues (all (L) or all (D)). a and d (shown with arrow) are hydrophobic α-amino acids. 3 to 8 heptad motifs represent a typical coiled-coil peptide.

B: Assembly to a trimer showing interactions of the hydrophobic residues a and d.

Figure 3:
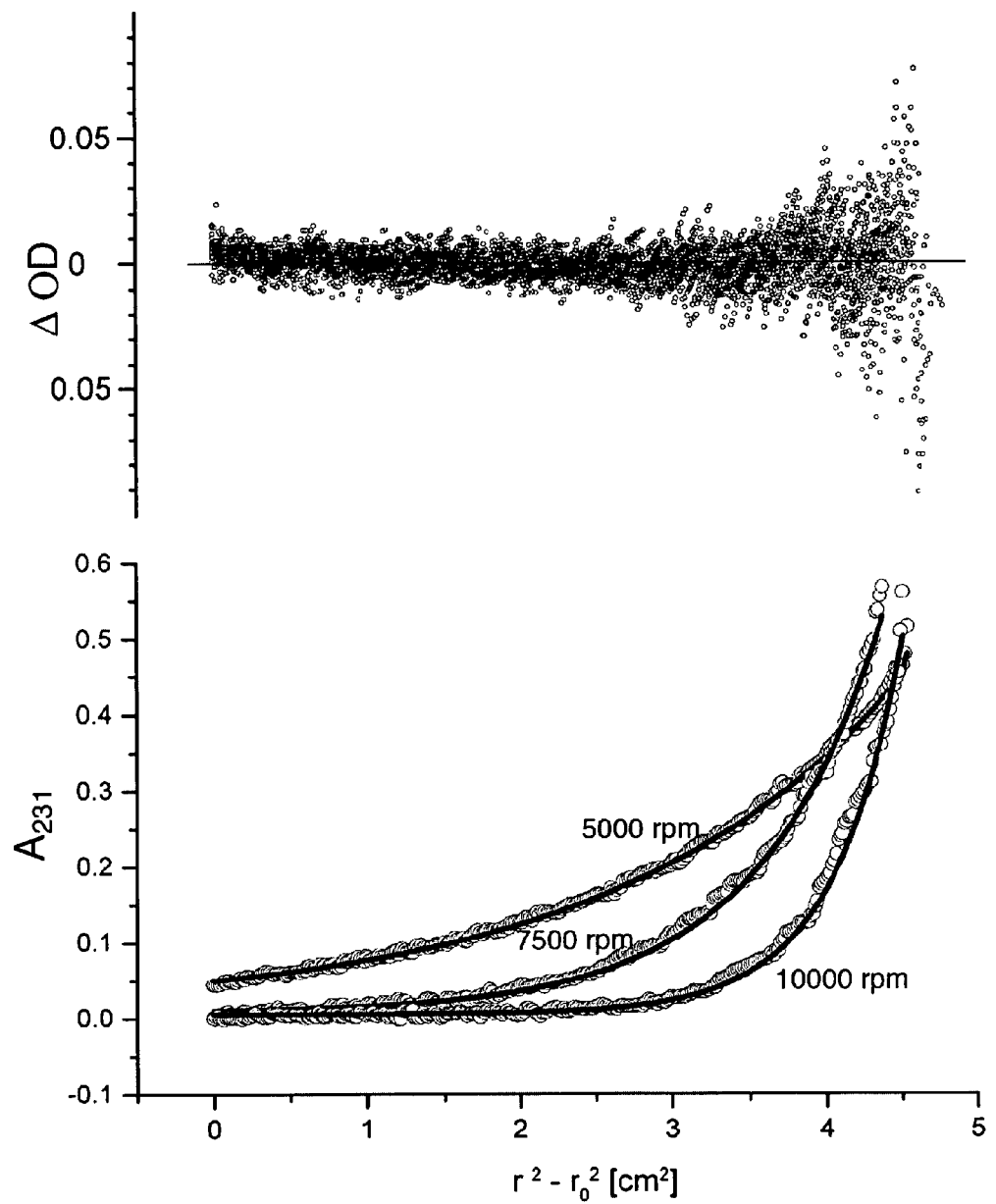

FIG. 3: Representative sedimentation equilibrium profile for lipopeptide 4 aggregates Lower panel: $A^{231}$, absorbance at 231 nm. Data points for 5000, 7500 and 10000 rpm. The lipoptide concentration was 24 µM in 0.01 M sodium phosphate, pH 7.4 containing 0.09 M sodium chloride (PBS).

Upper panel: Δ OD, optical density difference. Residuals to the global fit for 18 data sets at 24 and 48 µM and 3 rotor speeds.

Figure 4:
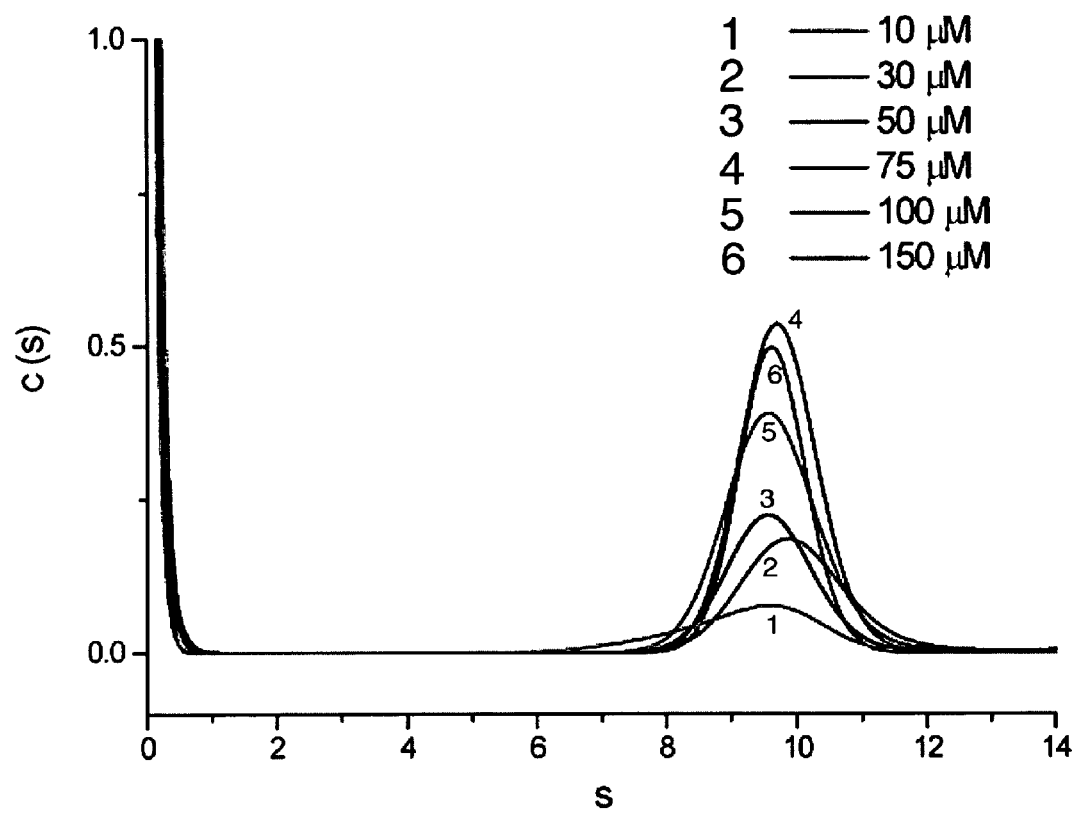

FIG. 4: Sedimentation velocity experiments for lipopeptide 4 aggregates at different concentrations c(s) apparent sedimentation coefficient distribution. All the distributions (for 10, 30, 50, 75, 100 and 150 µM) were centered between 9.5 and 10 S.

Figure 5:
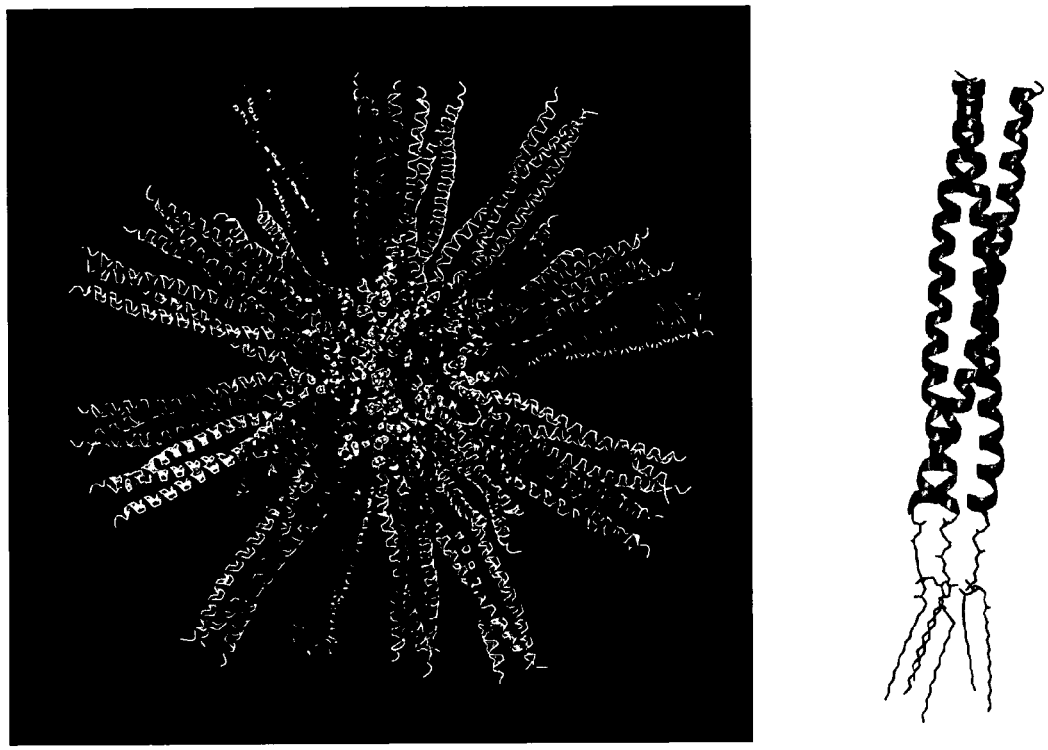

FIG. 5: Computer model for SVLP

SVLP formed from lipoprotein 4 composed of 24 subunits (HLBs). Each HLB (shown on right) is formed of three copies of the lipopeptide 4 to give a trimeric coiled coil.

Figure 6:
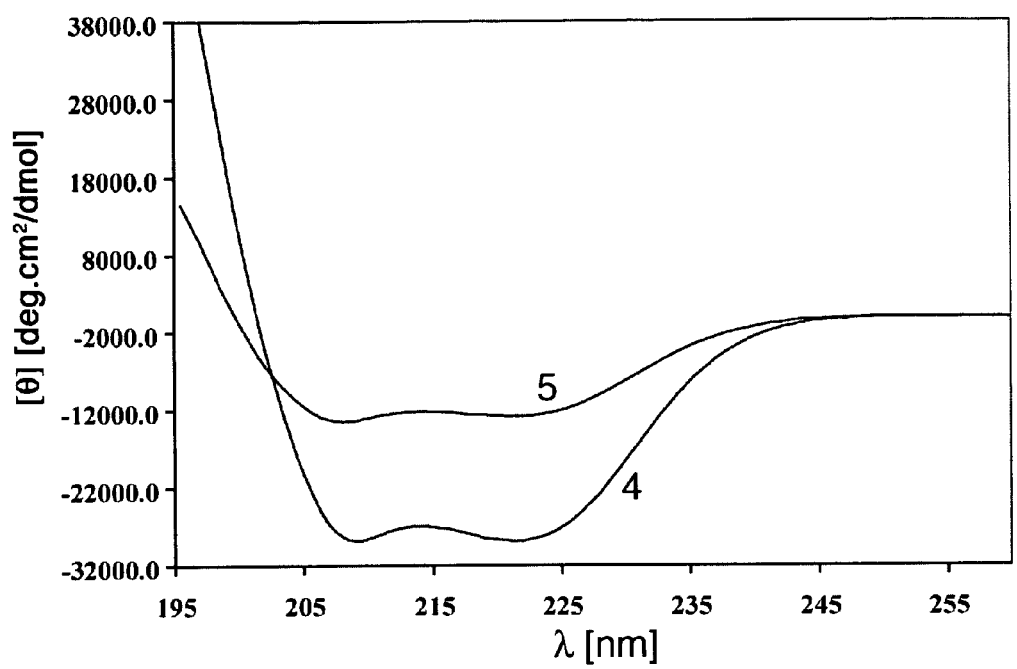

FIG. 6: CD spectra of lipopeptide 4 and peptide 5 aggregates

λ, wavelength in nm; Θ, mean residue ellipticity in deg.cm²/dmol.

lipopeptide 4 (20 µM) and peptide 5 (50 µM) in PBS at pH 7.4

Figure 7:
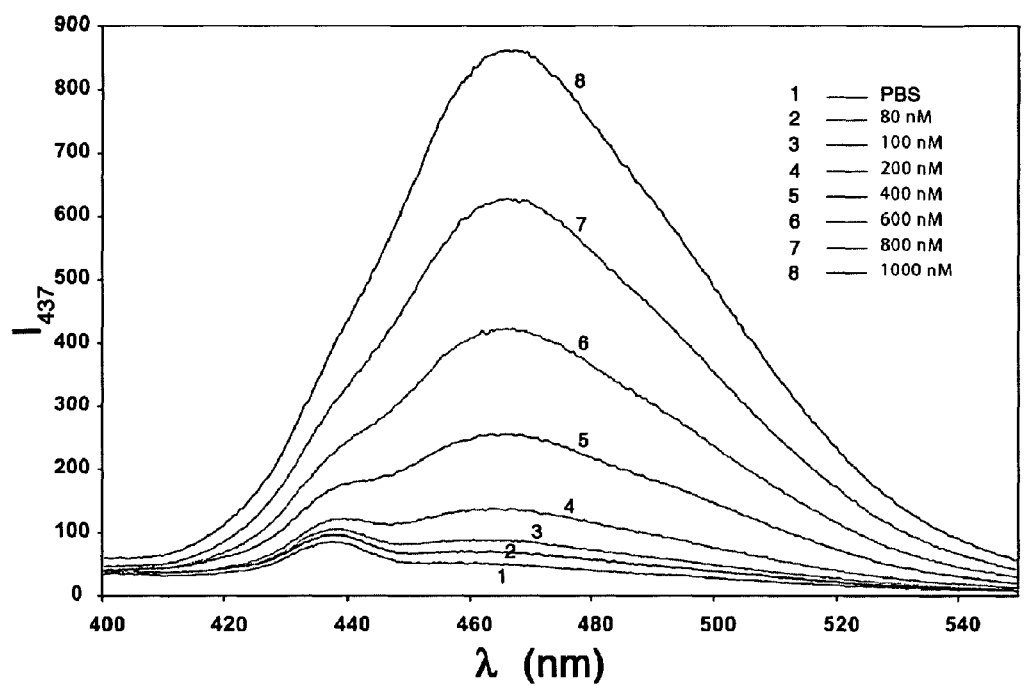

FIG. 7: Pyrene-3-carboxyaldehyde (PYCHO) emission spectra of lipopeptide 4 aggregates λ, wavelength in nm; $I_{437}$, fluorescence intensity at 437 nm (arbitrary units). The different curves correspond to buffer (PBS) and lipopeptide 4 concentrations of 80, 100, 200, 400, 600, 800 and 1000 nM.

Figure 8:
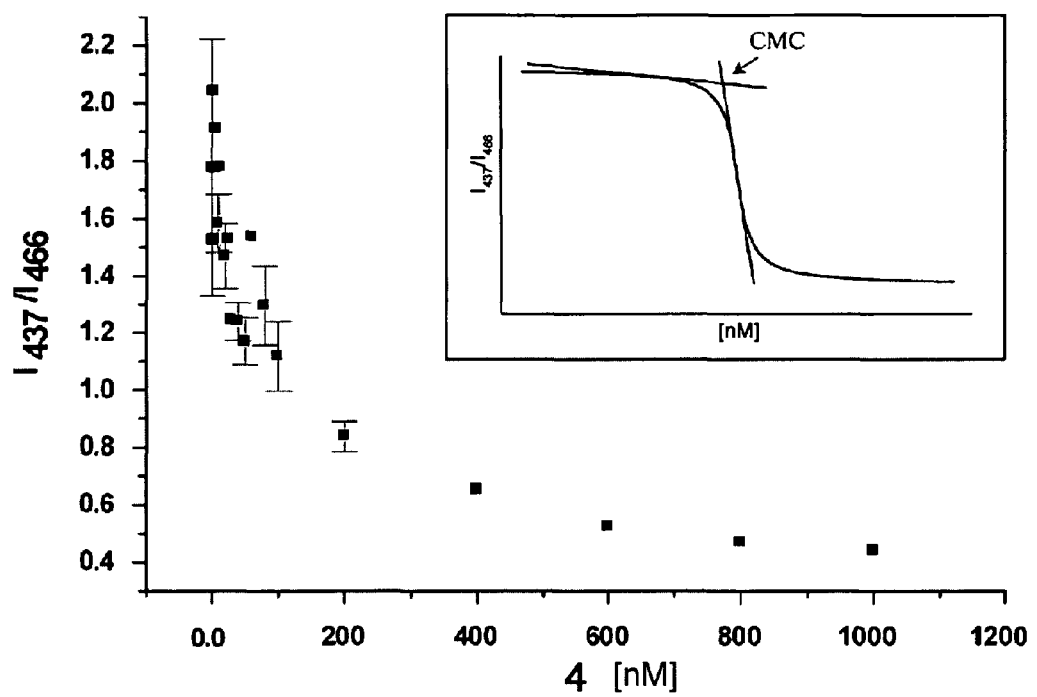

FIG. 8: Critical micelle concentrations of lipopeptide 4 aggregates

Fluorescence date were analysed to determine the critical micelle concentrations (CMC). Data are plotted as $I_{437}/I_{466}$ against concentration of lipopeptide 4 (nM). The insert shows how the CMC would be determined under ideal conditions.

Figure 9:
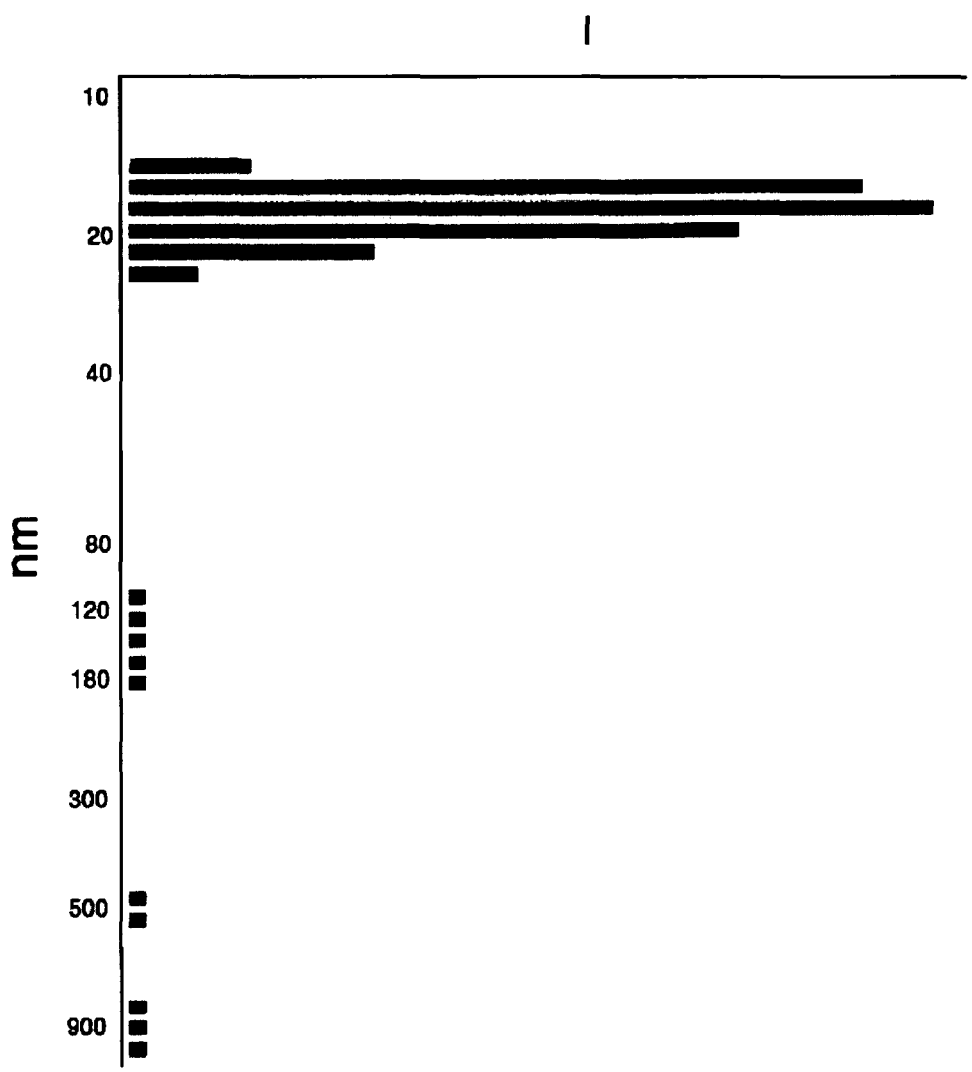

FIG. 9: Number-weighted NICOMP distribution analysis of DLS measurements for lipopeptide 4 aggregates 1.1 mM solution of lipopeptide 4 in TRIS buffer at pH 7.4 and 20° C. The mean diameter of the particle formed was ca. 17 nm.

Figure 10:
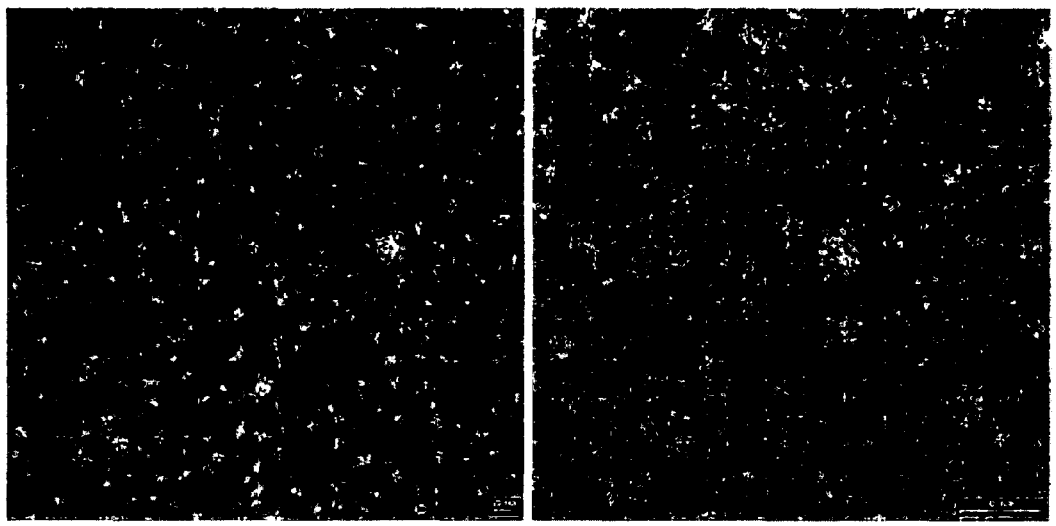

FIG. 10: Negative staining electron micrographs for lipopeptide 4 aggregates

SVLP formed by the lipopeptide 4 in TRIS buffer, pH 7.4. Left side scale bar 20 nm; right side scale bare 50 nm (enlargement). The star-like shape of the 15-20 nm particles and the high homogeneity of the sample can be clearly seen.

DETAILED DESCRIPTION OF THE INVENTION

The invention comprises lipopeptide building blocks (LBB) consisting of
a peptide chain (PC) comprising a coiled-coil domain, linked covalently to
a lipid moiety (LM) comprising three or preferably two long hydrocarbyl chains, and optionally linked to
an antigen (A).

The peptide chain (PC) comprises coiled-coil domains. Such coiled-coil domains will associate into a defined helical bundle, e.g. into a dimeric, trimeric, tetrameric, pentameric, hexameric or heptameric bundle. The peptide may contain between 12 and 120 amino acid residues, preferably between 21 and 80 amino acid residues. Coiled-coil domains contain multiple tandem repeat motifs, which as self-standing lipid-free peptides possess the property of self-assembly into a parallel coiled-coil helical bundle. The peptide chain (PC) must multimerize to form a parallel coiled-coil helical bundle of defined oligomerization state (e.g. dimer, trimer, tetramer, pentamer, hexamer or heptamer, in particular dimer, trimer, tetramer or pentamer). Preferred peptide sequences are non-human sequences to avoid the risk of autoimmune disorders when applied in the vaccination of humans.

The peptide chain may further comprise an amino acid sequence motif which includes one or more T-helper cell epitopes, and/or strings of polar residues that promote the solubility of the lipopeptide building block (LBB) in water.

The lipid moiety (LM) contains a lipid anchor with two or three, preferably two, long hydrocarbyl chains and a structure combining these hydrocarbyl chains and connect it to the peptide chain (PC), either directly or via a linker. Preferred lipid moieties are phospholipids containing two or three, preferably two extended hydrocarbyl chains.

"Long hydrocarbyl" means a straight alkyl or alkenyl group of at least 7 carbon atoms, for example straight alkyl or alkenyl consisting of between 8 and 50 C atoms, preferably between 8 and 25 C atoms. Alkenyl has preferably one, two or three double bonds in the chain, each with E or Z geometry, as is customarily found in natural fatty acids and fatty alcohols. Also included in the definition of "long hydrocarbyl" is branched alkyl or alkenyl, for example alkyl bearing a methyl or ethyl substituent at the second or third carbon atom counted from the end of the chain, as e.g. in 2-ethyl-hexyl.

Particular preferred lipid moieties according to the invention are those of formula $Z^1$ to $Z^8$ $Z^1$ $Z^2$ wherein $R^1$ and $R^2$ are long hydrocarbyl or long hydrocarbyl-C=O and Y is H or COOH, $Z^3$ wherein $R^1$, $R^2$ and $R^3$ are long hydrocarbyl or $R^1$ and $R^2$ are long hydrocarbyl-C=O and $R^3$ is H or acetyl, $Z^4$ $Z^5$ wherein $R^1$ and $R^2$ are long hydrocarbyl-C=O and n is 1, 2, 3 or 4, $Z^6$ wherein $R^1$ and $R^2$ are long hydrocarbyl, X is O or NH, and n is 1, 2, 3 or 4, or $Z^7$ $Z^8$ wherein $R^1$ and $R^2$ are long hydrocarbyl.

The lipid moiety contains at least two long hydrocarbyl chains such as found in fatty acids, e.g. as in $Z^1$ to $Z^8$. One preferred lipid moiety is a phospholipid of various types, e.g. of formula $Z^1$ or $Z^2$, that possess either ester or ether-linked extended alkyl or alkenyl chains, such as either enantiomer of 1,2-dipalmitoyl-sn-glycero-3-phosphoethanolamine, or achiral analogues such as 1,3-dipalmitoyl-glycero-2-phosphoethanolamine. A preferred lipid moiety is a tri- or di-palmitoyl-S-glycerylcysteinyl residue (type $Z^3$) or lipid moieties of types $Z^4$ to $Z^8$. Most preferred are the lipid moieties described in the Examples.

The peptide chain (PC) is covalently linked to the lipid moiety (LM) at or near one terminus, i.e. the N terminus or the C terminus, preferably the N terminus. The lipid moiety may be directly attached (1) or via a linker (2 or 3), wherein L means linker and X is O or NH.

(1)

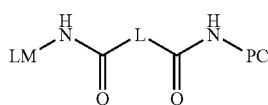
(2)

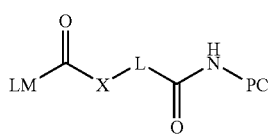
(3)

It will be apparent to those knowledgeable in this area, that a large variety of suitable linkers and coupling strategies exist, which include but are not limited to linkers based on dicarboxylic acid derivatives, linkers containing one or multiple ethylene glycol units, amino acid residues (including α-, β-, γ-, δ-amino acids etc.), or sugar (carbohydrate) units, or containing heterocyclic rings. Particular linkers considered are linkers $L^1$ to $L^{10}$, wherein n is between 1 and 20 and m is between 1 and 20, shown with the connecting functional group C=O or X wherein X is O or NH:

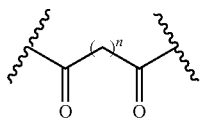
$L^1$

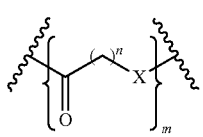
$L^2$

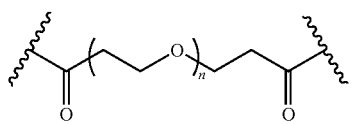
$L^3$

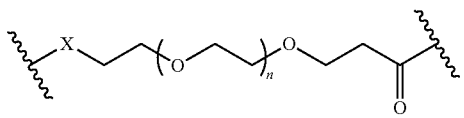
$L^4$

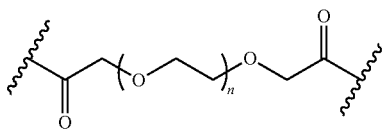
$L^5$

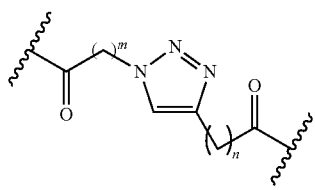
$L^6$

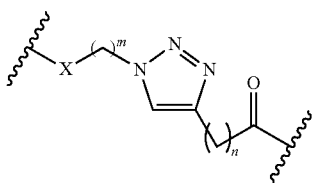
$L^7$

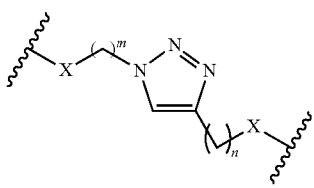
$L^8$

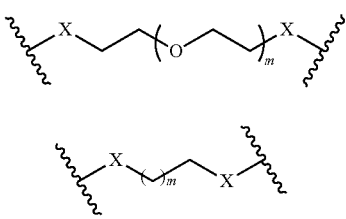
$L^9$

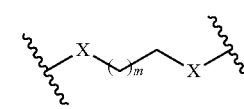
$L^{10}$

Most preferred are the linkers described in the Examples.

"Near one terminus" as understood in this connection means that the lipid moiety is bound to the first, second, third, fourth or fifth amino acid calculated from the N terminal or C terminal end, respectively, of the peptide. The lipid moiety may be attached to the backbone of the peptide structure or to the side chain of one of these amino acids near to the terminus.

"Antigens" as defined in the present invention are molecules capable of being bound by an antibody. The antigen may comprise a peptide, a protein or an epitope mimetic having one or more B-cell epitopes that are to be used to elicit an antigen-specific humoral immune response in an animal. Alternatively, the antigen may comprise a hapten or a carbohydrate. Suitable peptide and protein antigens comprise up to 150 amino acids and include glycopeptides and glycoproteins. Peptide and protein sequences may be so chosen as to elicit an immune response, for example against one or more varieties of infectious agents. Such antigens are well known in the art. An epitope mimetic is a molecule mimicking a natural peptidic or carbohydrate epitope, including peptidic compounds containing one or more non-natural amino acids, e.g. D-amino acids, β-amino acids, γ-amino acids, δ-amino acids, or ε-amino acids, and other replacements known in the art of epitope mimics. Preferred are conformationally constrained peptidomimetics, which are fixed in a protein-like conformation. Haptens refer to organic compounds with a molecular weight of less then 3,000, which do not elicit humoral immune responses by themselves, but will elicit an immune response once attached to a carrier. Exemplary haptens include drugs, hormones, toxins and carbohydrates.

Preferred are the antigens described in the Examples.

The antigen is covalently attached at or near the other end of the peptide chain, whereby "other" means the end of the peptide not carrying the lipid moiety. If the lipid moiety is connected at or near the N terminus of the peptide, then the antigen is bound at or near the C terminus. If the lipid moiety is connected at or near the C terminus of the peptide, then the antigen is bound at or near the N terminus.

One or more antigens may be conjugated to the coiled-coil domain of the peptide chain (PC), for example, through one or more of the side chains of amino acids in the coiled-coil peptide (e.g. lysine, or cysteine), or through the chain terminus of the peptide chain. The antigen carries a functional group suitable for conjugation to a functional group in one of the side chains or the terminus of the peptide chain. Preferred are antigens recognized by a B-cell receptor, or haptens, in order to elicit antigen-specific antibody-based immune responses.

"Coiled-coil domains" are designed by careful selection of appropriate amino acid sequences that form a thermodynamically stable, alpha-helical, parallel bundle of helices by spontaneous self-association.

A coiled-coil domain includes peptides based on canonical tandem heptad sequence repeats that form right handed amphipathic α-helices, which then assemble to form helical bundles with left-handed supercoils. Also included are peptides built from non-canonical, non-heptad-based repeats that form coiled-coils that are not necessarily left-handed or even regular supercoils.

Canonical coiled-coils occur widely in naturally occurring biologically active peptides and proteins, and have also been designed de novo. A set of rules has been elucidated for designing coiled-coil peptides that adopt helical bundles of defined oligomerization state, topology and stability (e.g. dimer, trimer, tetramer, pentamer, hexamer or heptamer). These rules allow designers to build a peptide sequence compatible with a given target structure. Most important, the sequences of canonical coiled-coil peptides contain a characteristic seven-residue motif, which is repeated typically 3-10 times. The positions within one heptad motif are traditionally denoted abcdefg, with mostly (but not exclusively) hydrophobic residues occurring at sites a and d and generally polar, helix-favoring residues elsewhere. Tandem heptad motifs along a peptide chain have an average separation between the a and d residues that allows them to fall on one face of the alpha-helix. When two or more helices pack together into a coiled-coil bundle the hydrophobic faces of the helices associate and wrap around each other in order to maximize contacts between hydrophobic surfaces (FIG. 2). The type of residue that may occur at each position within a heptad repeat will influence the stability and oligomerization state of the helical bundle. In general, mostly hydrophobic residues (Ala, Ile, Leu, Met, Val), or aromatic hydrophobic side chains (Phe, Trp and Tyr), are used at the a and d sites. The remaining b, c, e, f and g sites tend to be more permissive than the a and d sites, though polar and helix-favoring residues (Ala, Glu, Lys and Gln) are favored. The choice of residues at the a and d sites can influence the oligomerization state of the coiled coil (i.e. dimer vs. trimer). Thus, dimers are favored when non-β-branched residues (e.g. Leu) occur at the d positions; at these sites β-branched residues (Val and Ile) disfavor dimers. On the other hand, in dimers β-branched residues (Ile, Val) are preferred at the a sites. Another rule is that a=d=Ile or Leu favors trimers, which is useful in designing coiled coils that specifically form parallel trimers. These and other design rules are discussed in more detail in [Woolfson, D. N., Adv. Prot. Chem., (2005), 70, 79-112].

The heptad motif codes for amphipathic α-helices that oligomerize through their hydrophobic faces (FIG. 2). The coiled-coil domain includes at least three tandem heptad repeat motifs. The upper number of heptad repeats in each chain will influence the stability of the helical bundle. It is limited mainly by the feasibility of chemical synthesis of long peptides, but sequences containing more than three heptad repeats (e.g. four, five, six, seven and eight heptad repeats) are preferred. Examples discussed below form trimeric alpha-helical coiled-coils (see also FIG. 1), but the invention likewise concerns dimeric, tetrameric, pentameric, hexameric and heptameric coiled-coil domains.

Coiled-coil domains according to the invention may have longer repeat units, for example 11-residue repeats and 15-residue repeats such as are present in naturally occurring coiled-coils. Thus the helical bundles required for the formation of aggregate structures may also arise when using coiled-coil motifs with periodicities other than seven. Coiled coils with unusual periodicities are also possible. In many naturally occurring coiled coils the unbroken heptad repeat pattern may contain various discontinuities. Two common discontinuities are insertions of one residue into the heptad pattern, as well as insertions of three or four residues. For example, a one residue insertion is seen in the trimeric coiled coil of influenza hemagglutinin. Other naturally occurring coiled coils display a periodicity other than seven, for example, the regular periodicity of 11 residues (termed hendecads) found in the surface layer protein tetrabrachion of *Staphylothermus marinus*.

Other examples of coiled-coil peptide sequences occurring naturally in viral coat proteins are coiled-coil motifs forming trimeric helical bundles in the gp41 coat protein of HIV-1, and the F-glycoprotein of RSV. These coiled-coil domains are included in the definition of coiled-coil domain according to the invention.

The preferred coiled-coil peptides should contain between 3-8 tandemly linked heptad motifs. The heptad motifs within the coiled coil may have identical sequences (as in lipopeptide 8), or they may each have different sequences (as in lipopeptides 6 and 7). In all cases, the seven positions of the seven amino acid residues within one heptad motif are designated with letters: a b c d e f g. The coiled coil peptide, therefore, comprises an amino acid sequence having the positions (abcdefg)$_{3-8}$.

Preferred are coiled-coil peptide sequences containing between 3-8 tandemly linked heptad motifs, wherein positions a and d in each heptad motif (abcdefg) contain alpha-amino acids belonging to the Group 1 and/or to the Group 2 as defined hereinbelow. In addition, not more than two of all the a and d positions may be occupied by any amino acid residue belonging to the Group 3, and not more than one of all the a and d positions may be occupied by any amino acid residue belonging to the Group 4 or Group 5 or by glycine. In addition, in positions b, c, e, f and g, alpha-amino acids belonging to the Groups 3, 4 and 5 are preferred, but amino acids belonging to the Groups 1 and 2 are allowed, with the addition that not more than one of these positions within any one heptad motif may be glycine, but none may be proline.

Group 1 comprises alpha-amino acid residues with small to medium sized hydrophobic side chains $R^1$.

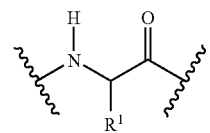

A hydrophobic residue $R^1$ refers to an amino acid side chain that is uncharged at physiological pH and that is repelled by aqueous solution. These side chains generally do not contain hydrogen bond donor groups, such as primary and secondary amides, primary and secondary amines and the corresponding protonated salts thereof, thiols, alcohols, ureas or thioureas. However, they may contain hydrogen bond acceptor groups such as ethers, thioethers, esters, tertiary amides, or tertiary amines. Genetically encoded amino acids in this group include alanine, isoleucine, leucine, methionine and valine.

Particular hydrophobic residues $R^1$ are lower alkyl, lower alkenyl, —$(CH_2)_a(CHR^2)_bOR^3$, —$(CH_2)_a(CHR^2)_bSR^3$, —$(CHR^2)OR^3$, —$(CH_2)_aSR^3$, —$(CH_2)_aR^4$, or —$CH(CF_3)_2$; wherein $R^2$ is lower alkyl; $R^3$ is lower alkyl; $R^4$ is cyclohexyl, cyclopentyl, or cyclobutyl; a is 1 to 4; and b is 0 or 1.

Group 2 comprises amino acid residues with aromatic or heteroaromatic side chains $R^5$.

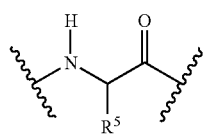

An aromatic amino acid residue refers to a hydrophobic amino acid having a side chain $R^5$ containing at least one ring having a conjugated aromatic π(pi)-electron system. In addition it may contain additional hydrophobic groups such as lower alkyl, aryl or halogen, hydrogen bond donor groups such as primary and secondary amines, and the corresponding protonated salts thereof, primary and secondary amides, alcohols, and hydrogen bond acceptor groups such as ethers, thioethers, esters, tertiary amides or tertiary amines. Genetically encoded aromatic amino acids include phenylalanine and tyrosine. A heteroaromatic amino acid residue refers to a hydrophobic amino acid having a side chain $R^5$ containing at least one ring having a conjugated aromatic pi-system incorporating at least one heteroatom such as O, S and N. In addition such residues may contain hydrogen bond donor groups such as primary and secondary amides, primary and secondary amines and the corresponding protonated salts thereof, alcohols, and hydrogen bond acceptor groups such as ethers, thioethers, esters, tertiary amides or tertiary amines. Genetically encoded heteroaromatic amino acids include tryptophan and histidine.

Particular aromatic or heteroaromatic side chains $R^5$ are —$(CH_2)_aR^6$, —$(CH_2)_cO(CH_2)_dR^6$, —$(CH_2)_cS(CH_2)_dR^6$, or —$(CH_2)_cNR^7(CH_2)_dR^6$; wherein $R^7$ is H, lower alkyl, aryl, or aryl-lower alkyl; $R^6$ is optionally substituted phenyl of formula —$C_6R^8R^9R^{10}R^{11}R^{12}$ or an aryl-or hetero-aryl group of one of the formulae H1 to H14

H1
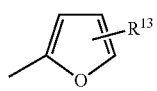

H2
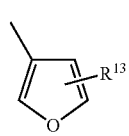

H3
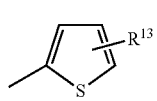

H4
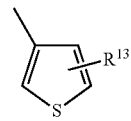

H5
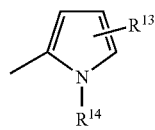

H6
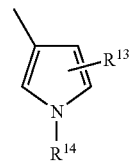

H7
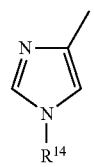

H8
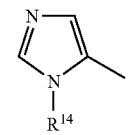

H9
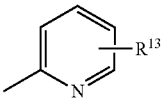

H10
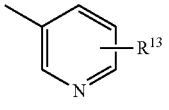

H11
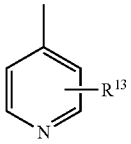

H12
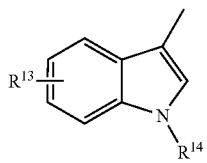

H13
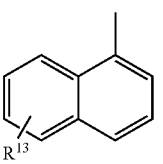

H14
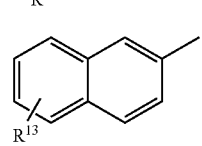

wherein each of $R^8$, $R^9$, $R^{10}$, $R^{11}$, $R^{12}$ is, independently of each other, H, F, Br, Cl, I, $NO_2$, $CF_3$, $NR^7R^{14}$, $NR^7COR^{14}$, lower alkyl, aryl, or $OR^7$; $R^{13}$ is H, Cl, Br, I, $NO_2$, lower alkyl, or aryl; $R^{14}$ is H, lower alkyl, or aryl; a is 1 to 4; c is 1 or 2; and d is 0 to 4.

Group 3 comprises amino acids containing side chains with polar non-charged residues $R^{15}$.

A polar non-charged residue $R^{15}$ refers to a hydrophilic side chain that is uncharged at physiological pH, but that is not repelled by aqueous solutions. Such side chains typically contain hydrogen bond donor groups such as primary and secondary amides, primary and secondary amines, thiols, and alcohols. These groups can form hydrogen bond networks with water molecules. In addition, they may also contain hydrogen bond acceptor groups such as ethers, thioethers, esters, tertiary amides, or tertiary amines. Genetically encoded polar non-charged amino acids include asparagine, cysteine, glutamine, serine and threonine.

Particular polar non-charged residues $R^{15}$ are $-(CH_2)_d$ $(CHR^{16})_bOR^{17}$, $-(CH_2)_d(CHR^{16})_bSR^{17}$, $-(CH_2)_a$ $CONR^{17}R^{18}$, or $-(CH_2)_aCOOR^{19}$; wherein $R^{16}$ is lower alkyl, aryl, aryl-lower alkyl, $-(CH_2)_aOR^{17}$, $-(CH_2)_a$ $NR^{17}R^{18}$, $-(CH_2)_aNR^{17}R^{18}$, or $-(CH_2)_aCOOR^{19}$; $R^{17}$ and $R^{18}$ are, independently of each other, H, lower alkyl, aryl, or aryl-lower alkyl, or $R^{17}$ and $R^{18}$ taken together are $-(CH_2)_e-$, $-(CH_2)_2-O-(CH_2)_2-$, or $-(CH_2)_2-$ $NR^{17}-(CH_2)_2-$; $R^{19}$ is lower alkyl, aryl, or aryl-lower alkyl; and wherein a, b and d have the meaning as defined above and e is 2 to 6.

Group 4 comprises amino acids containing side chains with polar cationic residues and acylated derivatives thereof, such as acylamino-derived residues and urea-derived residues $R^{20}$.

Polar cationic side chains $R^{20}$ refer to a basic side chain, which is protonated at physiological pH. Genetically encoded polar cationic amino acids include arginine, lysine and histidine. Citrulline is an example for a urea-derived amino acid residue.

Particular polar cationic residues and acylated derivatives thereof $R^{20}$ are $-(CH_2)_aNR^{17}R^{18}$, $-(CH_2)_aN=C$ $(NR^{21}R^{22})NR^{17}R^{18}$, $-(CH_2)_aNR^{21}C(=NR^{22})NR^{17}R^{18}$, $-(CH_2)_aNR^{21}COR^{19}$, or $-(CH_2)_aNR^{21}CONR^{17}R^{18}$; wherein $R^{21}$ is H or lower alkyl and $R^{22}$ is H or lower alkyl; and $R^{17}$, $R^{18}$, $R^{19}$ have the meaning as defined above and a is 1 to 4.

Group 5 comprises amino acids containing side chains with polar anionic residues $R^{23}$.

Polar anionic refers to an acidic side chain $R^{23}$, which is deprotonated at physiological pH. Genetically encoded polar anionic amino acids include aspartic acid and glutamic acid. A particular polar cationic residue $R^{23}$ is $-(CH_2)_aCOOH$ wherein a is 1 to 4.

Lower alkyl is $C_{1-7}$-alkyl, preferably $C_{1-4}$-alkyl, in particular methyl, ethyl, n-propyl, iso-propyl, n-butyl or iso-butyl. Aryl has 5 to 10 carbon atoms and is preferably phenyl or naphthyl.

More preferred are coiled-coil peptide sequences containing between 3 to 8 tandemly linked heptad motifs, wherein each heptad motif (abcdefg) may have any one of the following sequences:
1xx1xxx (referring respectively to the positions abcdefg);
1xx2xxx (referring respectively to the positions abcdefg);
2xx1xxx (referring respectively to the positions abcdefg); or
2xx2xxx (referring respectively to the positions abcdefg);
wherein 1 is a genetically encoded amino acid from group 1, 2 is a genetically encoded amino acid from group 2, and where x is a genetically encoded amino acid from groups 1, 2, 3, 4 or 5 or glycine.

Even more preferred are coiled coil peptide sequences identified in naturally occurring peptides and proteins, but excluding those of human origin. These are, for example, coiled coils identified in viral and bacterial proteins, including the following:

```
From influenza virus hemagglutinin (SEQ ID NO: 5):
GSTQAAIDQINGKLNRVIEKTNEKFHQIEKEFSEVEGRIQDLEKYVEDTK
CG;

from human immunodeficiency virus (SEQ ID NO: 6):
SGIVQQQNNLLRAIEAQQHLLQLTVWGIKQLQARILAVERYLGDCG;

from bovine immunodeficiency virus (SEQ ID NO: 7):
GGERVVQNVSYIAQTQDQFTHLFRNINNRLNVLHHRVSYLEYVEEIRQKQ
VFFGCG;

from feline immunodeficiency virus (SEQ ID NO: 8):
GGATHQETIEKVTEALKINNLRLVTLEHQVLVIGLKVEAMEKFLYTAFAM
QELGCG;

from equine infectious anemia virus
(SEQ ID NO: 9):
GGNHTFEVENSTLNGMDLIERQIKILYAMILQTHARVQLLKERQQVEETF
NLIGCG;

from simian immunodeficiency virus
(SEQ ID NO: 10):
GGAQSRTLLAGIVQQQQQLLDVVKRQQELLRLTVWGTKNLQTRVTAIEKYL
KDQAGCG;

from caprine arthritis encephalitis virus
(SEQ ID NO: 11):
GGSYTKAAVQTLANATAAQQDVLEATYAMVQHVAKGVRILEARVARVEAG
CG;

from Visna virus (SEQ ID NO: 12):
GGSLANATAAQQNVLEATYAMVQHVAKGIRILEARVARVEAIIDRMMVYQ
ELDCG;

from human parainfluenza-3 (SEQ ID NO: 13):
GGEAKQARSDIEKLKEAIRDTNKAVQSVQSSIGNLIVAIKSVQDYVNKEI
VGCG;
```

-continued from human parainfluenza-1 (SEQ ID NO: 14):
GGEAREARKDIALIKDSIIKTHNSVELIQRGIGEQIIALKTLQDFVNNEI
RGCG;

from human parainfluenza-2 (SEQ ID NO: 15):
GGKANANAAAINNLASSIQSTNKAVSDVITASRTIATAVQAIQDHINGAI
VNGCG;

from human parainfluenza-4a (SEQ ID NO: 16):
GGKAQENAKLILTLKKAATETNEAVRDLANSNKIVVKMISAIQNQINTII
QGCG;

from human parainfluenza-4b (SEQ ID NO: 17):
GGKAQENAQLILTLKKAAKETNDAVRDLTKSNKIVARMISAIQNQINTII
QGCG;

from Measles virus (SEQ ID NO: 18):
GGSMLNSQAIDNLRASLETTNQAIEAIRQSGQEMILAVQGVQDYINNELI
GCG;

from Mumps virus (SEQ ID NO: 19):
GGAQTNARAIAAMKNSIQATNRAVFEVKEGTQQLAIAVQAIQDHINTIMN
TQLNNMSCG from Bovine respiratory syncytial virus
(SEQ ID NO: 20):
GGAVSKVLHLEGEVNKIKNALLSTNKAVVSLSNGVSVLTSKVLDLKNYID
KEGCG;

from Ebola virus (SEQ ID NO: 21):
GGANETTQALQLFLRATTELRTFSILNRKAIDFLLQRWGGTCHILGCG;

from Marburg virus (SEQ ID NO: 22):
GGANQTAKSLELLLRVTTEERTFSLINRHAIDFLLTRWGGTCKVLGCG;

from Rous sarcoma virus (SEQ ID NO: 23):
GGANLTTSLLGDLLDDVTSIRHAVLQNRAAIDFLLLAHGHGCG;

from Staphylothermus marinus (SEQ ID NO: 24):
GSIINETADDIVYRLTVIIDDRYESLKNLITLRADRLEMIINDNVSTILA
SIGCG;

From SARS coronavirus (SEQ ID NO: 25):
GGNVLYENQKQIANQFNKAISQIQESLTTTSTALGKLQDVVNQNAQALNT
LVKQLSSNFGCG;

from DUF16 domain of MPN010 from Mycoplasma
pneumoniae (SEQ ID NO: 26):
GGTKTEFKEFQTVVMESFAVQNQNIDAQGEQIKELQVEQKAQGKTLQLIL
EALQGINKRLDNLESCG;

a heptameric coiled coil (SEQ ID NO: 27):
GGKVKQLADAVEELASANYHLANAVARLAKAVGERGCG;

a trimeric coiled coil (SEQ ID NO: 28):
GGIEKKIEAIEKKIEAIEKKIEAIEKKIEAIEKKIAKMEKASSVFNVVNS
KKKC
or a tetrameric coiled coil (SEQ ID NO: 29):
KLKQIEDKLEEILSKLYHIENELAKIEKKLAKMEKASSVFNVVKKC.

Most preferred are the coiled-coil peptide sequences described in the Examples.

In the design of the lipopeptide building block, additional residues not including said heptad repeats may be optionally added at either or both of the N- and C-termini of the coiled-coil peptide chain. These additional residues may, for example, act as a linker between the heptad repeat (coiled-coil) region and the lipid moiety and/or the optionally attached antigen. These additional residues may also include amino acid sequences comprising T-helper cell epitopes.

The synthesis of the lipopeptide building blocks (LBB) may make use of peptide synthesis methods and coupling procedures, which are well known in this area of synthetic chemistry. Typically solid-phase peptide synthesis is used to assemble the peptide chain. The lipid moiety can be coupled to a linker to give a lipid-linker intermediate. The lipid-linker can then be added by standard coupling methods to e.g. the free N terminus of the peptide still attached to the resin. Finally, treatment with trifluoroacetic acid (TFA) cleaves the fully assembled lipopeptide from the resin and removes all standard side chain protecting groups.

A di-palmitoyl-S-glycerylcysteinyl-moiety ($Z^3$) can be coupled directly to the N-terminus of the peptide chain without a linker. In the case of lipid moieties of type $Z^4$, a suitably Fmoc-protected amino acid, such as bis-Fmoc-2,4-diaminobutyric acid, can be added at the N-terminus of the chain in the final stage of assembly. After removal of the (Fmoc) protecting groups, the two free amino groups can be acylated with an appropriate fatty acid derivative. The lipopeptide product is formed after cleavage from the resin with TFA. Similar well-established synthetic strategies can be used to prepare lipopeptide building blocks containing other lipid moieties.

A variety of coupling or conjugation procedures may be used to attach antigens to the peptide chain, which will be well known to those knowledgeable in the field. Thus free amino groups in the side chains of amino acids in the peptide chain of the LBB may be coupled to reactive esters in the antigen (e.g. N-hydroxysuccinimide esters prepared from carboxylic acids); thiols in the peptide chain may be coupled to maleimide groups in the antigen; azides may be incorporated into the side chains of amino acid residues in the peptide chain and coupled to antigens containing acetylene groups using copper catalyzed cycloaddition reactions; and other nucleophiles (e.g. hydrazino, hydroxylamino, vic-aminothiol groups) in the peptide may be coupled to electrophiles (e.g. aldehydes, ketones, active esters) in the antigen. It will be obvious that it is possible, in principle, to reverse the positions of the two reactive groups in the peptide chain and antigen in order to achieve selective coupling.

Examples of lipopeptide synthesis illustrating these methods are described below.

Lipopeptide building blocks (LBB) as herein defined will self-assemble to helical lipopeptide bundles (HLB) and further to synthetic virus-like particles (SVLP). The self-assembly process in aqueous solution includes the rapid oligomerization of the coiled-coil domains in the LBB, to form a parallel coiled-coil bundle of alpha-helices of defined oligomerization state; referred to as a helical lipopeptide bundle (HLB). As a result the lipid moieties attached to the peptide chains within each HLB also aggregate at one end of the bundle. Furthermore, multiple copies of the antigen will then be presented on the surface of the HLB, i.e. the other, non-lipophilic end of the HLB. The self-assembly process may proceed further, resulting in the formation of synthetic virus-like particles (SVLP) (see FIG. 1). The process is driven by the self-association of the lipid tails attached to each building block, which then occupy the central lipid core of the SVLP. In this way, the peptide chains in each helical bundle are oriented outwards, towards the bulk solvent. The size and composition of the lipopeptide building block thus determines the final size and shape of the assemblies (SVLPs), the diameters of which are typically in the nanometer range (10-30 nm). The SVLPs represent a novel nanoparticle platform for the multivalent display of antigens, and for their delivery to immunocompetent cells and receptors.

The synthetic virus-like particles (SVLP) according to the invention are composed of protein and lipid components, as found in real viruses, have physical dimensions resembling those of some small viruses, have a lipid core and an external protein/peptide-based outer surface, but are totally of synthetic origin, i.e. are produced by chemical synthesis starting from lipopeptide building blocks (LBB) without using cell-based methods. They are not real viruses since they have no nucleic acid component and thus cannot replicate.

If antigens are attached to the lipopeptide building blocks (LBB), the resulting high surface density of antigens on HLBs and SVLPs, and also their molecular architecture, make these synthetic materials attractive for applications in the area of vaccine delivery. Having multiple copies of the antigen on the surface of the SVLP enhances B-cell receptor affinity to the antigen through an avidity effect, and facilitates uptake and presentation of the particle or its components by immunocompetent cells. The HLBs and SVLPs may, therefore, be viewed as macromolecular carriers, or delivery vehicles for antigens, for the purpose of raising efficient immune responses against the antigen in an animal. Of special importance, the use of HLBs and SVLPs as delivery vehicles for antigens allows the generation of efficient immune (antibody) responses in an animal without the use (co-injection) of potentially harmful adjuvants.

A unique combination of properties makes these HLBs and SVLPs ideal to elicit efficient immune responses in an animal, and hence for applications in vaccine discovery. B cell responses are initiated by the interaction of specific B-cell receptors on target B-cells with antigen, and in particular, by clustering of multiple B-cell receptors on the surface of B-cells through the binding of multivalent antigens. Having multiple copies of the antigen on the surface of an assembled particle is important to enhance receptor affinity through an avidity effect, and create clusters of antigen-bound B-cell receptors on the cell surface. The ability of the coiled-coil peptide to form helical bundles of defined oligomerization state is exploited to allow multivalent display of the covalently attached antigen. An antigen designed to interact with specific B-cell receptors on target B-cells, such as a hapten, peptide, protein or some other epitope mimetic, can be conjugated to the monomeric LBB. After self-assembly into a HLB and SVLP, the antigens are presented in multiple copies on the surface of the oligomeric assembly (see FIG. 1).

Viral and microbial coiled-coil sequences may contain T-helper cell epitopes. This can be exploited also in the present invention, since the coiled-coil carrier peptide being a component of LBB can be derived from natural sequences that contain T-helper cell epitopes. Alternatively, T-cell epitopes may be incorporated into, or appended to, designed or natural coiled-coil sequences.

The monomeric LBB contains a lipid moiety. Another purpose of the lipid is to facilitate presentation of the epitope to B cells, since it is known that antigens associated with membranes are particularly effective at activating B-cells and promoting B cell-driven T cell activation. The high local concentration of lipid moieties present within the assembled HLB and SVLP will facilitate interaction of the assembly with membranes and promote presentation of antigens to B cells. The lipid portion of the LBB may be derived from bacterially derived lipid moieties, such as the well-known lipopeptide Toll-like receptor ligands. A feature of the self-assembling lipopeptides incorporated in LBBs is that they may comprise components that enhance B-cell activation, as well as a mechanism for multivalent display of the antigen. Certainly, the HLBs and SVLPs are able to elicit strong antibody-based immune responses, and this leads to the further advantage that the use of toxic adjuvants during immunizations can be avoided.

It is a general feature of surfactant, detergent-like molecules possessing a polar head group and a non-polar, hydrophobic lipid tail, that they form thermodynamically stable aggregates such as micelles and vesicles in aqueous solution, with the extended hydrophobic regions clustered in the micelle core, sequestered away from contact with water, while the polar head groups interact with solvent. However, the HLBs and SVLPs of the present invention are not simply micelles. Their macromolecular architecture is maintained by a unique combination of non-covalent forces, namely, the forces driving assembly of the coiled-coil peptide domain into a helical bundle, coupled with the hydrophobic forces driving sequestration of the lipid tails in the interior of the particle.

The concentrations at which micelles begin to form, corresponding to the maximum concentration at which free monomer exists in solution, is the critical micelle concentration, or more generally, the critical aggregation concentration. The critical micelle concentration provides a measure of the thermodynamic stability of micelles. The critical micelle concentration value depends on the structure of the hydrophobic and hydrophilic parts of the amphiphilic molecule and external factors such as temperature and solvent composition. A low critical micelle concentration indicates a micelle stable at low surfactant concentration, which is of importance in biological applications, where the desired activity (e.g. cell targeting and delivery) is dependent upon retention of the micelle-like structure even after high overall dilution. SVLPs according to the invention remain thermodynamically stable in the low nanomolar region, indicating that they are ideal for the purpose of vaccine delivery. The high stability arises from the unique molecular architecture of SVLPs. Moreover, SVLPs can be made with relatively homogeneous size and shape distributions.

SVLPs according to the invention are not like liposomes, which possess a bilayer membrane structure enclosing an aqueous solution in the core. SVLPs will be more stable in vivo than liposomes as they do not expose large areas of lipid membrane to the aqueous exterior.

In contrast to virus-like particles of the prior art, the HLBs and SVLPs of the invention are artificial and all their components are produced by chemical synthesis, so avoiding the use of materials that must be made using biological methods. Although virus-like particles have been referred to as "synthetic", these particles are based on natural or genetically modified virus particles, or components thereof, made using recombinant DNA and cell-based methods, not materials produced by chemical synthesis. The design and composition of the SVLPs of the invention is also quite different from those of other nanoparticle assemblies, e.g. those based on gold clusters, quantum dots, dendrimers, recombinant proteins and liposomes.

Figure 1:
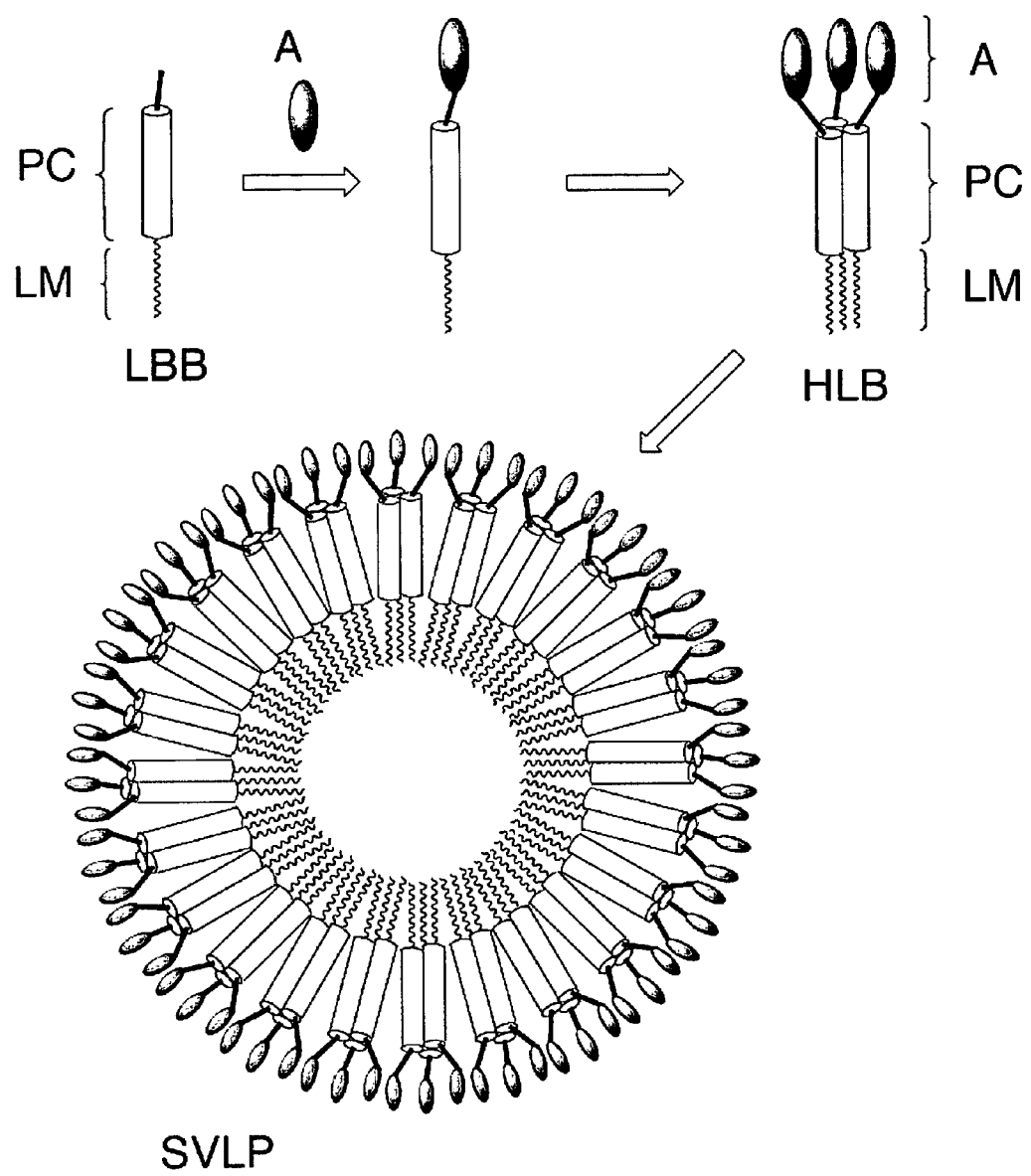
FIG. 1: Schematic representation of the components and assembly of a SVLP

The LBBs of the invention are designed in such a way that the coiled-coil domain in the lipopeptide will associate into a defined helical bundle (e.g. dimeric, trimeric, tetrameric, pentameric, hexameric or heptameric bundle of helices). This association leads to the formation of HLBs. The resulting helical lipopeptide bundles (HLBs) (e.g. a trimer is shown in FIG. 1) will self-assemble into a synthetic virus-like particle (SVLP) (macromolecular assembly) with dimensions on the nanometer scale. If antigens (in the form of peptides, proteins, peptidomimetics, carbohydrates or haptens) are attached to the LBB, multiple copies are presented on the surface of the HLB and SVLP.

Peptide sequences based on self (i.e. human) proteins are not suitable, since chronic autoimmune diseases can occur in humans due to immune reactions against human (self) proteins (e.g. Goodpasture's syndrome, an autoimmune disease caused when people develop antibodies against collagen).

The invention further relates to a pharmaceutical preparation comprising a synthetic virus-like particle carrying antigens as described herein. Pharmaceutical preparations for enteral administration, such as nasal, buccal, rectal or oral administration, and for parenteral administration, such as intravenous, intramuscular or subcutaneous administration, to warm-blooded animals, especially humans, are considered. Particularly preferred are preparations for parenteral administration. The preparations comprise the synthetic virus-like particle carrying antigens alone or, preferably, together with a pharmaceutically acceptable carrier. The dosage of the active ingredient depends upon the vaccination intended and upon the species, its age, weight, and individual condition, the individual pharmacokinetic data, and the mode of administration.

The pharmaceutical preparations comprise from approximately 1% to approximately 10% of the active ingredient. Unit dose forms for parenteral administration are, for example, ampoules or vials, e.g. vials containing from about 0.01 mg to about 1.0 g synthetic virus-like particle carrying antigens.

Preference is given to the use of solutions of the synthetic virus-like particle carrying antigens, and also suspensions or dispersions, especially isotonic aqueous solutions, dispersions or suspensions which, for example in the case of lyophilised compositions comprising the active ingredient alone or together with a carrier, for example mannitol, can be made up before use. The pharmaceutical preparations may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilising processes. The said solutions or suspensions may comprise viscosity-regulating agents.

For parenteral administration, aqueous solutions of the synthetic virus-like particle carrying antigens or aqueous injection suspensions that contain viscosity-regulating substances and, if desired, stabilizers, are especially suitable. The synthetic virus-like particle carrying antigens, optionally together with excipients, can also be in the form of a lyophilisate and can be made into a solution before parenteral administration by the addition of suitable solvents.

The invention further relates to the use of a synthetic virus-like particle carrying antigens as described herein as a vaccine. These vaccines are useful for inducing immune responses for the prevention or treatment of diseases, disorders or conditions, including infectious diseases, allergies, cancer, drug addiction, poisoning, and generally to efficiently induce antigen specific immune responses.

The invention further relates to a method of vaccination wherein an immunogenetically effective amount of a synthetic virus-like particle carrying antigens as described herein is administered to a patient in need thereof.

EXAMPLES

Abbreviations:
DCM, dichloromethane ($CH_2Cl_2$);
DIEA, diisopropylethylamine;
Boc, t-butoxycarbonyl;
DMF, N,N-dimethylformamide;
EDT, ethanedithiol;
Fmoc, 9-fluorenylmethoxycarbonyl;
HATU, 2-(1H-9-azabenzotriazole-1-yl)-1,1,3,3-tetramethyluronium hexafluorophosphate;
HBTU, 2-[1H-benzotriazole-1-yl]-1,1,3,3-tetramethyluronium hexafluorophosphate;
HOBt, N-hydroxybenzotriazole; Pbf, 2,2,4,6,7-pentamethyldihydrobenzofuran-5-sulfonyl;
NMP, N-methylpyrrolidone;
MBHA, methylbenzhydrylamine
PyBOP, (benzotriazol-1-yloxy)-tripyrrolidinophosphonium-hexafluorophosphate;
r.t., room temperature;
TIS, triisopropylsilane ($iPr_3SiH$);
Trt, trityl;
TFA, trifluoroacetic acid;
$t_R$, retention time.

Example 1

Lipopeptide 4

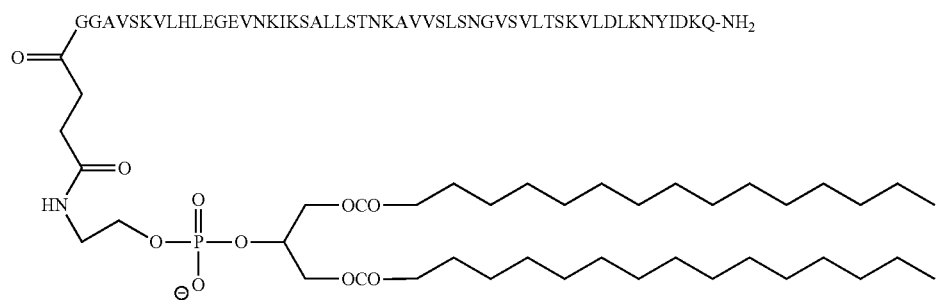

The primary sequence of SEQ ID NO:1 of the coiled-coil peptide 5 in this lipopeptide is derived largely from the RSV F-glycoprotein [Lawless-Delmedico, M. K., et al., Biochemistry, (2000), 39, 11684-11695]. This coiled-coil peptide contains five heptad repeats. Additional Gly residues have been added at the N terminus as a spacer, together with a linker derived from succinic acid to link the peptide N terminus to a phospholipid, thereby giving lipopeptide 4.

The synthesis of the peptide chain was performed on Rink amide MBHA resin using standard Fmoc chemistry. After completing chain assembly, the phospholipid-linker unit (1,3-dipalmitoyl-glycero-2-phosphoethanolamido-succinate (PE-succ-OH)) was coupled to the free N terminus of the peptide on the resin. The phosholipid was then cleaved from the resin and side chain protecting groups were removed by treatment with TFA/triisopropyl-silane/$H_2O$. After purification by reverse phase HPLC, the product was characterized by analytical reverse phase HPLC and electrospray MS (m calc. 6238.4; m/z obs. 1560.8 for $(M+4H)^{4+}$).

The 1,3-dipalmitoyl-glycero-2-phosphoethanolamido-succinate (PE-succ-OH) can be readily prepared by reacting 1,3-dipalmitoyl-glycero-2-phosphoethanolamine (Bachem) with succinic anhydride in the presence of a base such as triethylamine.

a) Peptide 5. The peptide chain was synthesized on Rink Amide MBHA resin (Novabiochem) on an ABI 433A peptide synthesizer using Fmoc chemistry. The amino acids used where Fmoc-Ala-OH, Fmoc-Asp(tBu)-OH, Fmoc-Asn(Trt)-OH, Fmoc-Gly-OH, Fmoc-Gln(Trt)-OH, Fmoc-Glu(tBu)-OH, Fmoc-His(Boc)-OH, Fmoc-Ile-OH, Fmoc-Leu-OH, Fmoc-Lys(Boc)-OH, Fmoc-Ser(tBu)-OH, Fmoc-Thr(tBu)-OH, Fmoc-Tyr(tBu)-OH, and Fmoc-Val-OH. The resin (500 mg; 0.4 mmol/g) was loaded with Fmoc-Gln(Trt)-OH using HBTU (3 eq.), HOBt (3 eq.) and DIEA (8 eq.) in DMF (5 ml). The unreacted free amines were acetylated using $Ac_2O$ capping solution ($Ac_2O$ (0.5 M), DIEA (0.125 M) and HOBt (0.015 M) in NMP; 2×15 ml for 30 minutes). Couplings were performed using a 5-fold excess (1 mmol) of each amino acid.

Following completion of the peptide chain assembly, the peptide chain was cleaved from the resin and deprotected with $TFA/iPr_3SiH/H_2O$ (95:2.5:2.5) (9 ml) for 3 h at r.t. After filtration and concentration in vacuo, the peptide was precipitated with cold $Et_2O$ (20 ml), centrifuged and decanted (repeated 3 times). Purification of the crude product by analytical HPLC($C_{18}$ column: Vydac 218TP54; 10 µm, 300 Å, 4.6× 250 mm; gradient: 5-100% acetonitrile in water+0.1% TFA, in 20 min at 1 ml/min; $t_R$=16 min) gave peptide 5 (10% yield) as a white powder. Analytical RP-HPLC($C_{18}$ column: Vydac 218TP54; 10 µm, 300 Å, 4.6×250 mm; gradient: 10-60% acetonitrile in water+0.1% TFA, in 35 min at 1 ml/min): $t_R$=26 min. ESI-MS ($MeOH/H_2O$ (1:1)+0.1% HCOOH; positive ion mode; m/z): 1822.8 $[M+3H]^{3+}$, 1367.3 $[M+4H]^{4+}$, 1094.2 $[M+5H]^{5+}$, 911.9 $[M+6H]^{6+}$(calc. MW: 5465.4 g/mol).

b) Lipopeptide 4. Assembly of the linear peptide chain on the resin was performed as described above for peptide 5. Following completion of the peptide chain assembly, 1,3-dipalmitoyl-glycero-2-phosphoethanolamido-succinate (PE-succ-OH) was coupled to the N-terminus on the resin. A solution of PE-succ-OH (190 mg, 240 µmol, 3 eq.), HATU (92 mg, 240 µmol, 3 eq.), HOAt (33 mg, 240 µmol, 3 eq.) and DIEA (110 µl, 640 µmol, 8 eq.) in DMF (5 ml), previously prepared, was added to the peptidyl resin (80 µmol). The reaction mixture was swirled overnight at r.t. The progress of the coupling was monitored by the Kaiser test. Following completion of the coupling, the resin was filtered and washed with DMF (3×5 ml), DCM (3×5 ml), and MeOH (3×5 ml). The lipopeptide was then cleaved from the resin and deprotected with $TFA/TIS/H_2O$ (95:2.5:2.5) (27 ml) for 3 h at r.t. After filtration and concentration in vacuo, the peptide was precipitated with cold $Et_2O$ (20 ml), centrifuged and decanted (repeated 3 times). Purification of the crude product by semi-preparative HPLC($C_4$ column: Vydac 214TP1010; 10 µm, 300 Å, 10×250 mm; gradient from 30-100% acetonitrile in water+0.1% TFA, in 15 min at 5 ml/min; $t_R$=14.4 min) gave lipopeptide 4 as a white powder. Analytical HPLC($C_4$ column: Vydac 214TP104; 10 µm, 300 Å, 4.6×250 mm; gradient: 10-100% acetonitrile in water+0.1% TFA, in 30 min at 1 ml/min): $t_R$=23.3 min. ESI-MS ($MeOH/H_2O$ (1:1)+0.1% HCOOH; positive ion mode; m/z): 2081.4 $[M+3H]^{3+}$, 1560.8 $[M+4H]^{4+}$, 1248.9 $[M+5H]^{5+}$ 1040.9 $[M+6H]^{6+}$(calc. MW: 6238.4 g/mol). $\epsilon_{276}$=1511 $M^{-1}$ $cm^{-1}$.

c) Biophysical Studies on Lipopeptide 4.

A key feature of this invention is that the lipopeptide, which is accessible by synthesis, can assemble spontaneously into a macromolecular assembly of defined structure and with the size of a virus-like nanoparticle. The lipopeptide 4 can be dissolved in buffered aqueous solution with shaking and the solution properties of the SVLPs can then be investigated. To demonstrate that such lipopeptides can form SVLPs, the particles arising from lipopeptide 4 have been characterized by various biophysical techniques, and are described here to illustrate the principle.

Sedimentation equilibrium ultracentrifugation experiments with lipopeptide 4 indicated that the particles had an apparent mass in the 400 kD range (FIG. 3). Triplicate data sets were collected at three rotor speeds, 5,000, 7,500 and 10,000 rpm, and at three concentrations, 24, 48 and 240 µM, for analysis. The data at the two lower lipopeptide concentrations were well fitted by a model that assumed the presence of a single, ideal species with an apparent molar mass of 451, 820±9,670 $g.mol^{-1}$. Inclusion of the data at the highest concentration (240 µM) resulted in an apparent mass of 431, 170±14,160 $g.mol^{-1}$ but the quality of the fit deteriorated, particularly close to the base of the ultracentrifugation cell. Deviation of the fit from the experimental data, however, did not have a form typical of the appearance of aggregated material but may have represented non-ideality at higher concentration.

Sedimentation velocity experiments were also performed and analysed in terms of the apparent sedimentation coefficient distributions, g(s*) [Stafford, W. F., Anal. Biochem., (1992), 203, 295-301], ls-g*(s) and c(s) [Schuck, P., Biophys. J., (2000), 78, 1606-1619]. Despite the different approaches, all methods gave relatively broad distributions centered on ~10 S. In an attempt to reconcile equilibrium and velocity data and to investigate the size distribution in more detail, Lamm equation modelling, as implemented by the Sedfit software [Schuck, P., Biophys. J., (2000), 78, 1606-1619] was used; typical c(s) profiles are shown in FIG. 4. The distributions are all centered between 9.5-10 S although there appears to be slight tailing to the low S side at low concentration, possibly due to artifacts. No significant statistical improvement was found when other models, involving discrete non-interacting species were tested. Inspection of the individual s values showed no apparent concentration dependence and global fitting of the data followed by Monte Carlo simulation gave a value of $s_{20,w}$=9.837±4.4·$10^{-3}$ S.

The chemical nature of the phospholipid and the apparent number of monomers involved in the major associated state (~72) suggest that, in the concentration range studied, the lipopeptide forms micelle-like structures and a model is proposed, in which approximately 24 subunits, each composed of a trimeric coiled-coil lipopeptide interact, forming a compact lipid core decorated by coiled-coil peptide chains. The size of the resulting particle is supported by the ultracentrifugation data. It is also proposed that the peptides are optimally distributed in space. In order to visualize such a spherical particle, a computer model was generated and is shown in FIG. 5. This shows the hydrophobic tails agglomerated in the center, and the trimeric helical coiled-coils extending like spikes out into solution. While geometries other than a perfect sphere might be possible, the model appears to reflect well the behaviour of the material in dilute solution under standard conditions.

To investigate the conformation of the peptide by circular dichroism (CD), the peptide 5, which has the same peptide sequence as lipopeptide 4 but lacks the phospholipid and linker, was analyzed. As expected in such a system, the peptide exhibited a CD spectrum that was both temperature and concentration dependent. It was highly α-helical at 1° C. and the thermal denaturation transition exhibited a mid point of ~40° C. at a peptide concentration of 35 µM. A peptide with a sequence similar to that of peptide 5 had been shown earlier to form a trimeric coiled-coil in equilibrium with the monomer in dilute aqueous solution [Lawless-Delmedico, M. K., et al., Biochemistry, (2000), 39, 11684-11695]. Peptide 5 differs from this peptide in that it has two additional N-terminal glycine residues and a free N terminus. However, the far UV CD spectrum (FIG. 6) at room temperature was similar for both peptides. Any minor differences were probably due to the simple addition of an aperiodic structure by the additional glycine residues and/or any further structural perturbation they might have induced. The spectrum is characteristic of a random-coil/α-helix equilibrium and spectral analysis using the CONTIN program [Provencher, S. W., Comp. Phys. Comm., (1982), 27, 229-242] gave values of 33%, 25% and 42% for α-helix, β-sheet and aperiodic structure, respectively.

The addition of a phospholipid moiety to peptide 5, forming lipopeptide 4, causes marked changes in the CD spectrum (FIG. 6) and the helix content rises to ~100% as judged by the CONTIN fit. Direct contributions of the phospholipid moiety to the spectrum were ignored and are likely to be small. The increase in helical content indicates that either the equilibrium situation found in the peptide alone is shifted to the more structured state, that there is a rearrangement to a different but highly structured state, or a combination of the two. In the light of the hydrodynamic results, reported above, it seems likely that the latter is the case, as this would account for the presence of relatively small species co-existing with much larger aggregates and probably forming a new equilibrium system.

The critical micelle concentration (CMC) was investigated using the fluorescence probe pyrene-3-carboxyaldehyde (PYCHO). The fluorescent properties of the probe are sensitive to the polarity of the solvent, and so the probe exhibits different fluorescent behaviour in a hydrophobic micellar medium compared to an aqueous medium. The dye dissolves preferentially in the hydrophobic interior of a micelle, and its fluorescence intensity is higher and the emission maximum is shifted to a longer wavelength relative to an aqueous environment. Emission spectra of the dye in the presence of the lipopeptide 4 showed a major peak at 466 nm and a minor peak at 437 nm, while the inverse behaviour was found in the absence of the micelle (FIG. 7).

The CMC was investigated by measuring the concentration dependence of fluorescence changes [Wilhelm, M., et al., Macromol., (1991), 24, 1033-1040; Astafieva, I., et al., Macromol., (1993), 26, 7339-7352], and was found to be <20 nM. However, the sensitivity and reliability of the method is very good for micellar systems with high CMC values, but it appears to be unsatisfactory for the precise determination of CMC values below 20 nM. Thus, the characteristics of the PYCHO fluorescence spectra in this system showed only small peak shifts at low concentrations (FIG. 7).

Emission spectra at 12 dilutions of the lipopeptide were measured in the 1 µM-3 nM range, and data were plotted as the ratio of the emission intensities, $I_{437}/I_{466}$, against the concentration. From the results (FIG. 8), it is apparent that the plateau region expected at peptide concentrations below the CMC has not been attained. At higher concentrations (400 nM to 1 µM) the beginning of a plateau is seen where increasing the monomer concentration simply leads to the formation of new oligomers. Hence, the changes in the PYCHO fluorescence spectra indicate that an oligomer is formed and that the CMC is very low (<20 nM).

The mean diameter of the SVLPs derived from this lipopeptide was calculated from dynamic light scattering (DLS) measurements using a number-weighted distribution analysis based on a mathematical model for spherical particles. The data are consistent with a mean diameter of about 17 nm (FIG. 9). The particle size by DLS was also measured at 40° C., where the particle size distribution became slightly narrower, indicating possibly a more homogeneous size distribution at physiological temperatures (data not shown).

Electron microscopy was used to visualize the lipopeptide SVLP. Negative staining of a 3 µM solution of the lipopeptide 4 in TRIS buffer at pH 7.4 was used to record transmission electron micrographs. The particles appear to be circular and star shaped (FIG. 10). Whether this reflects an underlying overall spherical or disk-like shape cannot be determined from the electron micrographs, but either structure would be indicative of a micelle-like system. The particles had an averaged diameter of 17 nm with a size distribution of approximately ±5 nm around the main population, depending on the method used to evaluate the micrographs. The high homogeneity in both size and shape of the sample was remarkable. Small numbers of larger assemblages, with diameters of between 25 nm and 40 nm could also be seen in the micrographs. This might have been an artifact of the technique used, since the particles could have adsorbed on the support in multiple layers. However, electron microscopy shows unequivocally the formation of stable nano-scale, star-like particles of regular shape and dimensions.

The star-like shape of the particles suggest an arrangement of lipopeptide monomers with the phospholipid chains pointing to the center of the particle (forming a hydrophobic core) and the hydrophilic peptide chains pointing outward as depicted in FIG. 5.

d) Experimental Section to Biophysical Studies on Lipopeptide 4.

Phosphate Determination

The assay was adapted from [Ames, B. N., Methods Enzymol., (1966), 8, 115-118] and was used to determine the concentration of the lipopeptide solutions used in the following experiments by estimating the total phosphate present in the phospholipid moiety. Materials used: A heating block capable of heating to 250° C. (e.g. Tecon programmable controller 630); temperature resistant borosilicate glass tubes for elemental analysis (60×7 mm Ø); and a water bath at 45° C.

1 mM Phosphate solution was prepared accurately from $KH_2PO_4$ (standard solution, 1 µl=1 nmol phosphate). Aliquots (usually from 10 to 80 µl depending on the estimated phosphate content of the sample) of the standard solution were added to a series of clean tubes in order to construct a calibration curve. The samples and the calibration standards were dried in the heating block (100° C.-120° C.) and when dry, 70 μl $H_2SO_4/HClO_4$ (1:1) was added to each tube and the tubes heated to 230-250° C. for 15-30 min.

A solution of 0.835% ascorbic acid/0.2% ammonium molybdate was prepared as follows; solutions of ascorbic acid (10% w/v) and ammonium molybdate (2.5% w/v) in doubly distilled $H_2O$ were prepared. Just before utilization, 1.67 ml of the ascorbic acid and 1.60 ml of the ammonium molybdate solutions were mixed together and the volume adjusted to 20 ml (sufficient for 12 samples).

After 15-30 min at 230-250° C. the samples were cooled to r.t., 1.6 ml of the assay solution was added with shaking and the samples were then incubated for 30 min at 45° C. A tube without sample or standard phosphate was treated identically throughout to provide a blank. Immediately after incubation, the absorbance at 820 nm of each sample was measured in a 1 cm cell. The concentration of the sample was interpolated from the standard curve.

Analytical Ultracentrifugation

Conventional sedimentation equilibrium and sedimentation velocity experiments were conducted using a Beckman XL-A analytical ultracentrifuge equipped with an AN60Ti rotor. Both double sector and 6-channel charcoal-filled Epon centerpieces were employed and fluorocarbon FC43 was used to provide a false bottom, where appropriate. A variety of rotor speeds, suitable for the particular experiment, were set and all measurements were carried out at 20° C. Experiments were carried out at several lipopeptide concentrations and buffers of either 10 mM Tris, pH 7.4, containing 90 mM sodium chloride or 10 mM sodium phosphate, pH 7.4, containing 90 mM sodium chloride were employed throughout. In sedimentation equilibrium runs radial data were collected at a spacing of 0.001 cm and at least 10 scans were averaged for each data set. Three such data sets were acquired at each speed and concentration. Equilibrium was confirmed by the superimposition of data collected at suitable time intervals. Sedimentation velocity data were acquired at a radial spacing of 0.005 cm with an interval between scans of 2-4 minutes. The additivity principle was used to calculate separately the apparent partial specific volume of the lipid ($v_{20}$=0.934 $cm^3g^{-1}$) and peptide ($v_{20}$=0.726 $cm^3g^{-1}$) moieties from their group contributions [Cohn, E. J., et al., in Proteins, amino acids and peptides as ions and dipolar ions, Hafner publishers, New York (1943), p. 370-381; Hoeiland, H., in Thermodynamic Data for Biochemistry and Biotechnology, Springer-Verlag, Berlin, (1986), p. 17-44; Traube, I., Ann. Chem. Liebigs, (1891), 265, 27; Laue, T. M., in Analytical Ultracentrifugation in Biochemistry and Polymer Science, Royal Society of Chemistry publishers, Cambridge, (1992)]. The partial specific volume of lipopeptide 4 ($V_{20}$=0.781 $cm^3g^{-1}$) was approximated as the mass-weighted average of the values of the two components. Buffer densities were computed from standard tables [Laue, T. M., in Analytical Ultracentrifugation in Biochemistry and Polymer Science, Royal Society of Chemistry publishers, Cambridge, (1992)]. The software packages Sedfit and Sedphat [Schuck, P., Biophys. J., (2000), 78, 1606-1619] were used for the analysis of velocity data while the Ultrascan program was used to analyse sedimentation equilibrium data [Demeler, B., UltraScan 5.0, (2001)].

Circular Dichroism Spectroscopy

Far ultraviolet circular dichroism (CD) spectra were measured at r.t. using a Jasco J-715 spectropolarimeter and a 0.1 cm path length quartz cell. Peptide 5 solution (50 μM) and lipopeptide 4 solution (35.7 μM) were prepared in TRIS buffer (10 mM TrisHCl, 90 mM NaCl, pH 7.4) and concentrations were determined by phosphate or amino acid analysis, as appropriate. Scan speeds of 10-100 nm/min, 1-2 second response times and a 1 nm spectral bandwidth were employed and spectra were collected at a minimum resolution of 0.5 nm. After subtraction of the blank, the spectral values were reported as mean residue ellipticity [deg. $cm^2$/dmol] and the lipid moiety was ignored when calculating the mean residue molecular weight.

CD spectra of low concentration samples of lipopeptide 4 (2-40 μM) were measured at 20° C. with a Jasco J-810 spectropolarimeter using a 1 cm path length quartz cell. Lipopeptide solutions were prepared in PBS (10 mM $Na_2HPO_4$, 90 mM NaCl, pH 7.4) and concentrations were determined by phosphate analysis. Scan speeds of 10 nm/min, 4 second response time and a 2 nm spectral bandwidth were employed and spectra were collected at a minimum resolution of 0.5 nm. Data were elaborated as described above.

Fluorescence: Critical Micelle Concentration (CMC)

The fluorescent probe pyrene-3-carboxyaldehyde (PYCHO) was used for the determination of the critical micelle concentration (CMC) [Turro, N. J., Macromolecules, (1984), 17, 2123-2126; Ananthapadmanabhan, K. P., et al., Langmuir, (1985), 1, 352-355]. Fluorescent spectra were obtained on a Perkin Elmer LS55 luminescence spectrometer. Emission spectra of pyrene-3-carboxyaldehyde were measured from 400-550 nm at 20° C. They were obtained by exciting the samples at 380 nm with a 300 nm/min scan speed, 4 nm excitation slit width and 9 nm emission slit width, each scan accumulated four times and averaged. Lipopeptide 4 solutions were prepared using HBS pH 7.4 (10 mM Hepes, 90 mM NaCl) previously saturated with PYCHO (solution concentration<$10^{-6}$ M). The fluorescence spectra were measured at 12 peptide concentrations between 1 μM and 5 nM, and sample concentrations were determined using the phosphate assay. Lipopeptide concentrations in the low nM (50 nM-3 nM) range were prepared using a 1/10 dilution of the saturated PYCHO solution in HBS buffer. Data were analyzed with Origin (v7.0) software and the relative intensity ratio $I_{437}/I_{466}$ of the emission spectra was plotted against the sample concentration in order to extrapolate the CMC value.

Dynamic Light Scattering (DLS)

Light scattering measurements were performed on a NICOMP submicron particle sizer (model 370). Lipopeptide 4 samples were prepared in TRIS buffer (10 mM, 90 mM NaCl, pH 7.4) and sample concentrations were determined using the phosphate assay. A 1.1 mM solution of lipopeptide 4 was filtered through a 0.45 μM Millipore filter, which yielded a 1.05 mM sample. Light scattering measurements were performed on this solution at 20° C., 30° C. and 37° C. The measurements at 20° C. were performed at times t=0, 20 and 90 min., at 30° C. and at 37° C. at times t=0 and 90 min. Elaboration of the data was performed with a NICOMP multi-component fitting model that assumes the presence of ideal spherical particles.

Electron Microscopy

Carbon coated 400 mesh copper grids, rendered hydrophilic in oxygen plasma, were used for a preliminary structural analysis by transmission electron microscopy (TEM). A small drop of lipopeptide 4 solution (4 μM in TRIS buffer pH 7.4) was applied to the hydrophilic C-support and after 20 sec, most of the solution was removed so that only a very thin layer remained on the grid. The grid was then washed, by touching the surface with a drop of water. The excess of water was blotted away and the grid was immediately stained, by touching the surface with a drop of 2% aqueous uranyl acetate. After removal of the staining solution, the grid was allowed to dry. Micrographs were recorded in a Zeiss EM 912 electron microscope (Zeiss AG, Oberkochen, BRD) using a 1 k×1 k slow scan CCD camera (Proscan, Munich, BRD).

Example 2

Lipopeptide 6

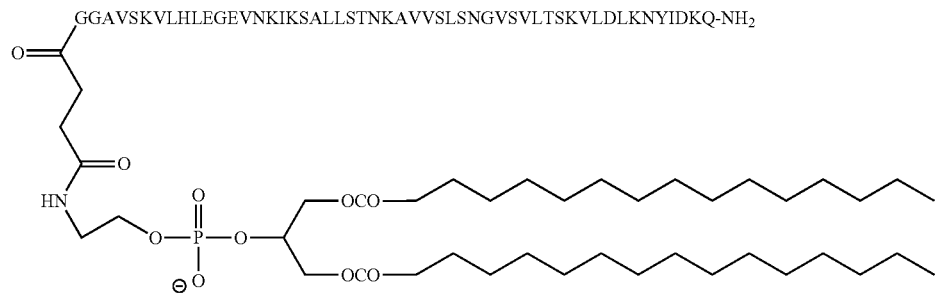

Lipopeptide 6 is identical to 4 except that an additional Cys is added at the C terminus of SEQ ID NO:1. The side chain of this Cys can be used to conjugate the lipopeptide to an antigen.

The 53-mer peptide was synthesized on Rink amide MBHA resin, using Fmoc chemistry, as above for peptide 5, with also Fmoc-Cys(Trt)-OH. Upon completion of the synthesis, a sample of the resin was treated with TFA. The product was then analyzed by reverse phase HPLC on a $C_{18}$ column (Zorbax Eclipse XDB-C18; 4.6 mm×250 mm, 5 μm, 80 Å) using a gradient of 5 to 50% acetonitrile in water (+0.1% TFA) over 18 min then to 100% acetonitrile in water (+0.1% TFA) over 4 min. Retention time=19.6 min. ESI-MS: (m/z): 1393.2 $[M+4H]^{4+}$; 1115.0 $[M+5H]^{5+}$; 929.1 $[M+6H]^{6+}$; 796.8 $[M+7H]^{7+}$($M_{meas}$=5569.6±0.01%; $M_{calc.}$=5569.6). Since the correct linear peptide was present on the resin, the phospholipid 1,3-dipalmitoyl-glycero-2-phosphoethanolamido-succinate (PE-succ-OH) was coupled to the N terminus of the remaining resin-bound peptide using PyBOP (3 eq.) and DIEA (8 eq.) in DMF:$CH_2Cl_2$ (2:1) at r.t. for 16 h. The completion of the coupling was confirmed by a negative Kaiser test. The resulting resin-bound conjugate was finally cleaved from the resin and deprotected using TFA/$H_2O$/TIS/EDT 92.5:2.5:2.5:2.5 for 3 h. The TFA phase was concentrated in vacuo, then the crude deprotected lipopeptide was precipitated by addition of cold $iPr_2O$. After centrifugation, the pellet was washed twice with $iPr_2O$ and dried under high-vacuum. The product was dissolved in $H_2O$/MeCN/DMF 4:4:2 and purified by reverse phase HPLC on a $C_4$ semi-preparative column (Interchrom UP5WC4-25M; 10 mm×250 mm, 10 μm, 300 Å) using a gradient of 50 to 100% aceto-nitrile in water (+0.1% TFA) over 15 min. The fractions containing the product were lyophilized to give the conjugate 6. The conjugate 6 was analyzed by reverse phase HPLC on a $C_4$ analytical column (Interchrom UP5WC4-25QS; 4.6 mm×250 mm, 10 μm, 300 Å) using a gradient of 50 to 100% acetonitrile in water (+0.1% TFA) over 20 min: purity>98%. $t_R$=17.2 min. ESI-MS (positive mode) (m/z): 1587.7 $[M+4H]^{4+}$; 1269.6 $[M+5H]^{5+}$; 1058.3 $[M+6H]^{6+}$; 907.0 $[M+7H]^{7+}$($M_{meas}$=6342.9±0.01%; $M_{calc.}$=6342.6).

Example 3

Lipopeptide 7

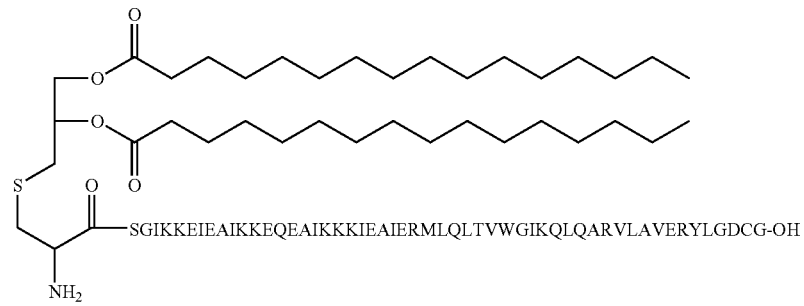

The peptide portion (SEQ ID NO:2) of this molecule contains a designed coiled-coil heptad repeat sequence fused to a natural coiled-coil sequence taken from the gp41 protein of the HIV-1 strain JR-FL. The coiled-coil sequence is, therefore, part natural and part designed. In addition, the dipeptide -SG- is added at the N terminus to act as a short spacer before the lipid, and at the C terminus the dipeptide -CG- is attached, so that the thiol group in the Cys residue can be used for conjugation to an antigen.

(+0.1% HCOOH) over 10 min.: $t_R$=5.47 min.; m/z=1342.5 $[M+5H]^{5+}$, 1118.9 $[M+6H]^{6+}$, 959.3 $[M+7H]^{7+}$, 893.4 $[M+8H]^{8+}$, 746.6 $[M+9H]^{9+}$. MALDI-TOF: m/z calculated for $C_{308}H_{532}N_{76}O_{82}S_3$: 6704.9; m/z found: 6704.7 $[M]^+$.

Example 4

Lipopeptide 8

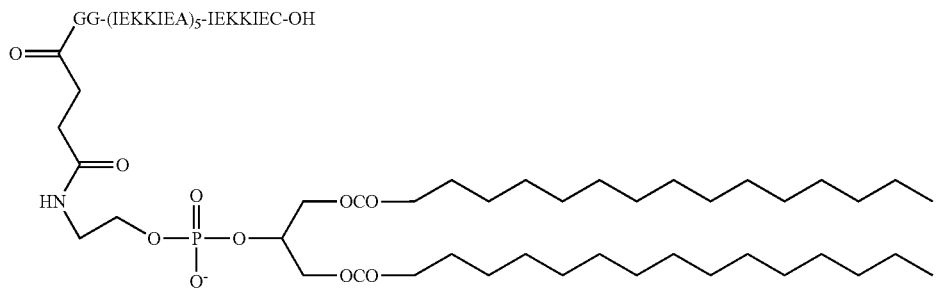

The peptide was assembled using HBTU/HOBt/DIEA for activation, and Fmoc-Gly-loaded 2-chlorotrityl chloride resin (0.34 mmol/g, 500 mg). The amino acids used were Fmoc-Ala-OH, Fmoc-Arg(Pbf)-OH, Fmoc-Asp(tBu)-OH, Fmoc-Cys(Trt)-OH, Fmoc-Gly-OH, Fmoc-Gln(Trt)-OH, Fmoc-Glu(tBu)-OH, Fmoc-His(Boc)-OH, Fmoc-Ile-OH, Fmoc-Leu-OH, Fmoc-Pro-OH, Fmoc-Lys(Boc)-OH, Fmoc-Met-OH, Fmoc-Ser(tBu)-OH, Fmoc-Tyr(tBu)-OH, Fmoc-Trp(Boc)-OH and Fmoc-Val-OH. A six-fold excess of Fmoc amino acids and 8 equivalents of DIEA were used. After each coupling cycle, remaining free amino groups were capped with $Ac_2O$/HOBt/DIEA. After assembly and removal of the terminal Fmoc group, the resin was washed with DMF (5×6 ml), i-PrOH (5×6 ml) and n-hexane (4×6 ml) and dried. For coupling of the lipid moiety, the resin (957 mg) was swelled for 30 min in $CH_2Cl_2$. A solution of Fmoc-Cys((RS)-2,3-di(palmitoyloxy)-propyl)-OH (Fmoc-Pam$_2$Cys-OH, 174 mg), PyBOP (101 mg) and HOBt (26 mg) in $CH_2Cl_2$/DMF 2:1 (3.5 ml) was added, followed by DIEA (1.6 equiv.). The mixture was gently agitated for 18 h on a shaker at r.t. The resin was washed with $CH_2Cl_2$ (5×6 ml) and DMF (5×6 ml). The Fmoc protecting group was removed by treatment with 20% (v/v) piperidine in DMF (6×2 ml for 2 min.). Deprotection was monitored by UV absorption at 301 nm. The resin was washed with DMF (5×10 ml), i-PrOH (5×6 ml) and n-hexane (4×6 ml) and $CH_2Cl_2$ (2×6 ml). The peptidyl resin was treated with 0.6% TFA in $CH_2Cl_2$ (4×4.5 ml for 2 min.), followed by a $CH_2Cl_2$ wash. The filtrates were combined and evaporated under reduced pressure. Subsequently, the side-chain protecting groups were removed by treatment with TFA/EDT/thioanisole/phenol/$H_2O$/TIS 69:10:10:5:3.5:1 (9.85 ml) with gentle agitation for 2 h at r.t. The deprotected peptide was precipitated in $iPr_2O$ pre-cooled to $-20°$ and washed 3× with $iPr_2O$ (15 ml). The precipitate was allowed to air-dry overnight and the coiled-coil lipopeptide was purified by RP-HPLC on a C4 preparative column (Interchrom) using a gradient of 30 to 100% MeCN in $H_2O$ (+0.1% TFA) over 28 min. Yield: 45 mg. RP-HPLC (Interchrom $C_4$ column, 50 to 100% MeCN in $H_2O$ (0.1% TFA) over 12.5 min.): purity>97%, $t_R$=11.92 min. LC-MS: $C_8$ column, 30 to 100% MeCN in $H_2O$ Lipopeptide 8 contains a designed coiled-coil (SEQ ID NO:3) coupled through a short linker at the N-terminus to a phospholipid.

The peptide (SEQ ID NO:3) was assembled using Fmoc chemistry and HBTU/HOBt/DIEA for activation and 2-chlorotrityl chloride resin (0.42 mmol/g, 595 mg, 0.25 mmol scale). The amino acids used were Fmoc-Ala-OH, Fmoc-Glu(tBu)-OH, Fmoc-Ile-OH, Fmoc-Lys(Boc)-OH and Fmoc-Cys(Trt)-OH. A four-fold excess of Fmoc-protected amino acids and 6 equivalents of DIEA was used. After each coupling cycle, remaining free amino groups were capped with $Ac_2O$/HOBt/DIEA. After assembly of the peptide chain and removal of the terminal Fmoc group, the resin was washed with DMF (5×6 ml), i-PrOH (5×6 ml) and n-hexane (4×6 ml) and dried in vacuo. To couple the lipid moiety, resin (250 mg) was swelled for 30 min in DCM. A solution of PE-succ-OH (113 mg), PyBOP (66 mg) and HOBt (17 mg) in DCM/DMF 1:2 (4.5 ml) was added, followed by DIEA (31 µl, 300 µmol, 6.0 equiv.). The mixture was gently agitated for 16 h on a shaker at r.t. The resin was washed with DMF (5×6 ml) and DCM (2×6 ml). The peptidyl resin was treated with 0.6% TFA in DCM (4×4.5 ml for 2 min.), followed by a DCM wash. The filtrates were combined and evaporated under reduced pressure. The side-chain protecting groups were then removed by treatment with TFA/EDT/thioanisole/$H_2O$/TIS 75:10:10:4:1 (10 ml) with gentle agitation for 2 h at r.t. The deprotected peptide was precipitated with $iPr_2O$ pre-cooled to $-20°$, and washed 3× with $iPr_2O$. The lipopeptide 8 was purified by reverse phase-HPLC on a C4 preparative column (Interchrom) using a gradient of 30 to 100% MeCN in $H_2O$ (+0.1% TFA) over 28 min. Yield: 15 mg. RP-HPLC (Interchrom $C_4$ column, 50 to 100% MeCN in $H_2O$ (0.1% TFA) over 12.5 min.): purity>96%, $t_R$=12.54 min. ESI-MS: m/z calculated for $C_{267}H_{474}N_{57}O_{79}PS$: 5810.0; m/z found: 1453.3 $[M+4H]^{4+}$, 1162.5 $[M+5H]^{5+}$.

Example 5

Antigen V3SS Bearing a 4-Maleimidobutyryl-Hydrazinoglycinyl Group, 12

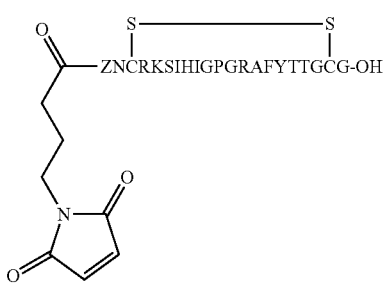

The disulfide bridged peptide called V3SS is taken largely from the so-called V3-loop of the HIV-1 gp120 glycoprotein. This sequence (SEQ ID NO:4) represents the so-called principal neutralizing determinant on gp120, and has been extensively investigated as a potential HIV-1 vaccine candidate [Huang, C.-C., et al., Science, (2005), 310, 1025-1028; Pantophlet, R., et al., Annu. Rev. Immunol., (2006), 24, 739-769]. The disulfide-bridged peptide V3SS is, therefore, an epitope mimetic of the V3 loop in gp120.

At the N-terminus of V3SS (SEQ ID NO:4), a hydrazinoglycine (Z) residue has been added, so that the nucleophilic hydrazino group can be used to couple the peptide to the LBB. The peptide chain was assembled on 2-chlorotrityl chloride resin using standard solid-phase methods and Fmoc chemistry. A tri-Boc-protected hydrazinoglycine residue was added at the N-terminus. After cleavage from the resin and full deprotection, the disulfide bond was introduced by air oxidation. Finally, the linker N-hydroxysuccinimidyl-4-maleimidobutyrate (HMB) was reacted regiospecifically with the hydrazino-group at the N-terminus to give the product 12.

The linear peptide Z-NCRKSIHIGPGRAFYTTGCG (Z added to SEQ ID NO:4), wherein Z means —NHNHCH$_2$CO— was synthesized on an Applied Biosystems ABI 433A peptide synthesizer using standard Fmoc chemistry and 2-chlorotrityl chloride resin. After loading with Fmoc-Gly-OH, the following side-chain protected amino acids were used for the synthesis: Fmoc-Ala-OH, Fmoc-Asn(Trt)-OH, Fmoc-Arg(Pbf)-OH, Fmoc-Cys(Trt)-OH, Fmoc-Gly-OH, Fmoc-His(Trt)-OH, Fmoc-Pro-OH, Fmoc-Ile-OH, Fmoc-Lys(Boc)-OH, Fmoc-Ser(tBu)-OH, Fmoc-Thr(tBu)-OH and Fmoc-Tyr(tBu)-OH. As N-terminal residue, Boc-protected hydrazinoglycine was coupled by treating the resin with a solution of tri-Boc-hydrazinoacetic acid (3 eq.), PyBOP (3 eq.) and DIEA (8 eq.) in DMF (5 ml) for 3 h. The resin was then filtered and washed with DMF (5×) then CH$_2$Cl$_2$ (5×). The peptide was cleaved from the resin and deprotected by treating the resin with TFA/H$_2$O/iPr$_3$SiH/ethanedithiol 92.5:2.5:2.5:2.5 (15 ml) for 2.5 h. The resin was removed by filtration, and after concentration of the filtrate in vacuo, the crude deprotected linear peptide was precipitated by addition of cold iPr$_2$O. After centrifugation, the pellet was washed twice with iPr$_2$O and dried under high-vacuum to give a white solid. The product was purified by reverse phase HPLC on a C$_{18}$ preparative column (Zorbax Eclipse XDB-C18; 21.2 mm×250 mm, 7 μm, 80 Å) using a gradient of 10 to 50% acetonitrile in water (+0.1% TFA) over 16 min, to afford the pure linear peptide, in the reduced dithiol form. This peptide was analyzed by reverse phase HPLC(C$_{18}$ analytical column Zorbax Eclipse XDB-C18; 4.6 mm×250 mm, 5 μm, 80 Å) using a gradient of 5 to 50% acetonitrile in water (+0.1% TFA) over 20 min: purity>98%; t$_R$=14.2 min. MALDI-TOF (m/z): 2211.2 [M+1H]$^{1+}$ (M$_{meas.}$=2210.2±0.01%; M$_{calc.}$=2210.4).

For oxidation (disulfide bridge formation), a solution of linear peptide (20 mg) in H$_2$O (20 ml) was stirred under air at r.t. for 48 h. The corresponding disulfide bridged peptide was directly purified by reverse phase HPLC on a C$_{18}$ preparative column (Zorbax Eclipse XDB-C18; 21.2 mm×250 mm, 7 μm, 80 Å) using a gradient of 12 to 40% acetonitrile in water (+0.1% TFA) over 16 min to afford 15 mg of oxidized peptide. The oxidized (disulfide bridged) peptide was analyzed by reverse phase HPLC(C$_{18}$ analytical column Zorbax Eclipse XDB-C18; 4.6 mm×250 mm, 5 μm, 80 Å) using a gradient of 5 to 50% acetonitrile in water (+0.1% TFA) over 20 min: purity>98%; t$_R$=14.2 min. MALDI-TOF (m/z): 2209.0 [M+1H]$^{1+}$(M$_{meas.}$=2208.0±0.01%; M$_{calc.}$=2208.4).

The disulfide bridged peptide (30 mg) in H$_2$O (30 ml) was dissolved in H$_2$O (3 ml) and the pH was adjusted to pH 6 using NaOH (0.2 N). To this was added a solution of N-hydroxysuccinimidyl-4-maleimidobutyrate (HMB) (3 eq., 11 mg) in THF (450 μl) and the reaction mixture was stirred at r.t. for 2 h. The solution was then diluted with H$_2$O/TFA 0.1% (2 ml) and the product was purified by reverse phase HPLC on a C$_{18}$ preparative column (Zorbax XDB-C18; 21.2 mm×250 mm, 7 μm, 80 Å) using a gradient of 10 to 50% MeCN in water (+0.1% TFA) over 16 min, to afford 21 mg of peptide 12. The peptide 12 was analyzed by reverse phase HPLC on a C$_{18}$ column (Zorbax Eclipse XDB-C18; 4.6 mm×250 mm, 5 μm, 80 Å) using a gradient of 5 to 50% acetonitrile in water (+0.1% TFA) over 20 min: purity>98%; t$_R$=14.7 min. MALDI-TOF (m/z): 2374.3 [M+1H]$^{1+}$ (M$_{meas.}$=2373.3±0.01%; M$_{calc.}$=2373.4).

Example 6

Antigen LY-CH Bearing a 4-Maleimidobutyryl Group, LY-CH-HMB

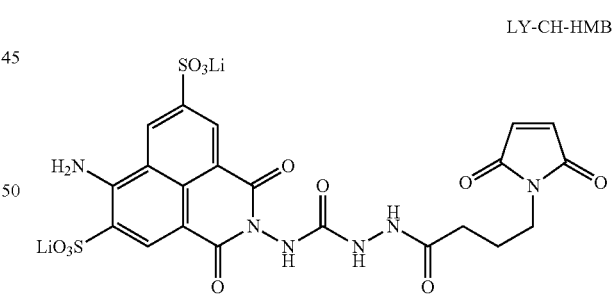

As in Example 5, the HMB linker was coupled to a small organic molecule hapten, the yellow dye called Lucifer Yellow-CH (LY-CH) to give the conjugate LY-CH-HMB.

Lucifer yellow-CH (LY-CH)(Fluka, Buchs, Switzerland, 12.5 mg) was dissolved in H$_2$O/CH$_3$CN (1 ml, 4:1) and the pH of the solution was adjusted to 6.5 with 0.2 N NaOH. To this solution was added a solution of N-hydroxysuccinimidyl-4-maleimidobutyrate (HMB) (15 mg, 2 eq.) in THF (400 μl) and the reaction mixture was stirred at r.t. for 6 h. After dilution with H$_2$O/TFA 0.1% (2 ml), the product was directly purified by reverse phase HPLC on a C$_{18}$ preparative column (Zorbax; 21 mm×250 mm, 10 µm, 120 Å) using a gradient of 5 to 50% acetonitrile in water (+0.1% TFA) over 15 min to afford 9.6 mg of LY-CH-HMB as a yellow solid. ESI-MS (m/z): 608.0 [M–H]⁻, 630.9 [M+Na–2H]⁻(negative ion mode).

Example 7

Conjugate LBB6-12

The peptide 12 (Example 5, 5.9 mg) was dissolved in H₂O/CH₃OH 4:1 (750 µl) and the pH of the solution was adjusted to 6.5 with NaOH (0.2 N). To this was added a solution of lipopeptide 6 (Example 2, 6.6 mg) in H₂O/CH₃OH 1:1 (800 µl) and the reaction mixture was stirred under inert atmosphere at r.t. for 2 h. After dilution with H₂O/TFA 0.1% (2 mL), the product was directly purified by reverse phase HPLC on a C₄ semi-preparative column (Interchrom UP5WC4-25M; 10 mm×250 mm, 10 µm, 300 Å) using a gradient of 50 to 100% MeCN in water (+0.1% TFA) over 15 min to afford 4 mg of LBB6-12. The conjugate was analyzed by reverse phase HPLC on a C₄ analytical column (Interchrom UP5WC4-25QS; 4.6 mm×250 mm, 10 µm, 300 Å) using a gradient of 50 to 100% acetonitrile in water (+0.1% TFA) over 20 min: purity>98%. $t_R$=15.4 min. MALDI-TOF (m/z): 8717.4 [M+1H]¹⁺($M_{meas.}$=8716.4±0.01%; $M_{calc.}$=8716.3).

Example 8

Conjugate LBB6-LY-CH

To a stirred solution of lipopeptide 6 (Example 2, 1.1 mg, 177 nmol) in H₂O/MeCN/TFE 1:4:1 (600 µl) was added dropwise a solution of LY-CH-HMB (Example 6, 440 µg) in H₂O/MeCN 1:1 (400 µl). The pH was carefully adjusted to pH 6.3 with 0.01 N NaOH and the mixture was stirred vigorously at r.t. for 2 h. Since the lipopeptide 6 and the lucifer yellow conjugate have an identical retention time on C₄ and C₈ RP-HPLC columns for a variety of H₂O/MeCN gradients, the reaction was followed by monitoring the disappearance of the lipopeptide 6 using ESI-MS. Upon completion of the reaction, the suspension was diluted by addition of 0.1% TFA (500 µl) and the adduct was separated from excess LY-CH-HMB by semi-preparative reversed phase HPLC on a C₄ column (Interchrom, UP5WC4-25M, 10 mm×250 mm, 10 m, 300 Å pore size, A=H₂O+0.1% TFA, B=MeCN+0.1% TFA, 50 to 100% B in 16.5 min.). The LBB6-LY-CH conjugate eluted as a sharp peak with $t_R$=13.38 min. Yield: 1.0 mg (82%). The product was analyzed by reversed phase HPLC on a C₄ analytical column (Interchrom; 4.6 mm×250 mm, 10 m, 300 Å) and by LC-MS (Zorbax C₈, ion source, detector). Analytical RP-HPLC (C₄ column, A=H₂O+0.1% TFA, B=MeCN+0.1% TFA, 50 to 100% B in 13 min.): Purity: >95%. $t_R$=13.0 min. LC-MS (C₈ column, A=H₂O+HCOOH, B MeCN+HCOOH, 30 to 100% B in 10 min): retention time=7.73 min. m/z: 1392.4 [M+5H]⁵⁺, 1160.3 [M+6H]⁶⁺, 994.3 [M+7H]⁷⁺(m/z calculated for $C_{307}H_{514}N_{74}O_{99}PS_3Li$: 1392.2 [M+5H]⁵⁺, 1160.3 [M+6H]⁶⁺, 994.7 [M+7H]⁷⁺).

Example 9

Conjugate LBB7-12

To a stirred solution of lipopeptide 7 (Example 3, 3.5 mg) in MeCN/H₂O/TFE 4:1:1 (1.2 ml) was added a solution of 12 (Example 5, 3.7 mg) in MeCN/H₂O 1:1 (400 µl). The pH was carefully adjusted to pH=6.0 with 0.1 N NaOH. The mixture was stirred for 2 h at r.t. After completion of the reaction (detected by LC-MS using a C8 column), the conjugate LBB7-12 was directly purified by semi-preparative RP-HPLC on a C4 column (Interchrom) using a gradient of 30 to 100% MeCN in H₂O (+0.1% TFA) over 17 min. Yield: 4.1 mg (87%). RP-HPLC(C₄ column, 50 to 100% MeCN in H₂O (0.1% TFA) over 12.5 min.): purity>97%, retention time=10.72 min. LC-MS (C₈ column, 30 to 100% MeCN in H₂O (+0.1% HCOOH) over 10 min.): $t_R$=5.53 min., m/z=1010.4 [M+9H]⁹⁺, 909.8 [M+10H]¹⁰⁺, 827.2 [M+11H]¹¹⁺, 758.3 [M+12H]¹²⁺, 700.0 [M+13H]¹³⁺. MALDI-TOF: m/z calculated for $C_{409}H_{685}N_{109}O_{112}S_5$: 9082.0; m/z found: 9082.8 [M]⁺, 4542.1 [M]²⁺.

Example 10

Conjugate LBB7-LY-CH

The synthesis and purification of LBB7-LY-CH was performed as described for LBB7-12 in Example 9 using lipopeptide 7 (3.0 mg) and LY-CH-HMB (Example 6, 1.1 mg). Yield: 2.8 mg (86%). RP-HPLC (Interchrom C₄ column, 50 to 100% MeCN in H₂O (0.1% TFA) over 12.5 min.): purity>96%, $t_R$=11.91 min. LC-MS: C₈ column, 66 to 100% MeCN in H₂O (+0.1% HCOOH) over 5 min.: $t_R$=2.7 min., m/z=1464.9 [M+5H]⁵⁺, 1220.7 [M+6H]⁶⁺, 1046.5 [M+7H]⁷⁺, 915.9 [M+8H]⁸⁺. MALDI-TOF: m/z calculated for $C_{329}H_{549}N_{82}O_{94}S_5Li$: 7324.8; m/z found: 7336.6 [M–Li+Na]⁺, 7320.4 [M]⁺, 3660.0 [M]²⁺.

Example 11

Immunizations

One important application of HLBs and SVLPs is in the delivery of vaccine components to the immune system in order to raise immune responses. Upon immunization of animals with antigen-loaded HLBs or SVLPs, efficient antigen-specific immune responses should be elicited. In order to demonstrate that this is possible, rabbits were immunized with LBB6-12, LBB6-LY-CH, LBB7-12 and LBB7-LY-CH. Furthermore, the first three conjugates were tested with and without Freund's complete/incomplete adjuvant. DLS studies indicated that each conjugate formed HLBs or SVLPs by spontaneous self-assembly in aqueous solution.

Rabbits (groups of two) were each immunized with 150 µg of one conjugate, reconstituted and equilibrated for at least 1 h at r.t. in either 400 µl PBS (10 mM sodium phosphate, 154 mM NaCl, pH 7.2), or with Freund's adjuvant (Freund's complete adjuvant (FA) for primary and Freund's incomplete adjuvant (FIA) for booster immunizations). Immunizations were performed on days 0, 28 and 56. Sera were collected on days 14, 38 and 66. The sera were analyzed by enzyme-linked immunosorbent assay (ELISA), to detect antibodies that bind to the conjugates used for immunizations. The results are shown in Table 1.

TABLE 1

Immunogenicity of conjugates.

| | | log₁₀ (Endpoint titers) [b] | | |
|---|---|---|---|---|
| Conjugate used [a] | Rabbit | 1° | 2° | 3° |
| LBB6-12 + FA(FIA) | 1a | 3.51 | 4.41 | 5.01 |
| LBB6-12 + FA(FIA) | 1b | <1.70 | 4.51 | 5.41 |
| LBB6-12 | 2a | 3.51 | 5.01 | 5.01 |

TABLE 1-continued

Immunogenicity of conjugates.

| | | log₁₀ (Endpoint titers) [b] | | |
|---|---|---|---|---|
| Conjugate used [a] | Rabbit | 1° | 2° | 3° |
| LBB6-12 | 2b | 2.00 | 3.81 | 4.71 |
| LBB6-LY-CH + FA(FIA) | 3a | 4.11 | 5.11 | 5.71 |
| LBB6-LY-CH + FA(FIA) | 3b | 3.51 | 4.41 | 5.31 |
| LBB6-LY-CH | 4a | 3.90 | 5.11 | 5.71 |
| LBB6-LY-CH | 4b | 4.20 | 5.11 | 5.40 |
| LBB7-12 + FA(FIA) | 5a | 2.30 | 3.20 | 3.51 |
| LBB7-12 + FA(FIA) | 5b | 2.90 | 3.81 | 4.11 |
| LBB7-12 | 6a | 3.81 | 4.41 | 4.41 |
| LBB7-12 | 6b | 3.51 | 4.11 | 4.11 |
| LBB7-LY-CH | 7a | 2.90 | 4.41 | 4.41 |
| LBB7-LY-CH | 7b | <1.70 | 3.51 | 4.11 |

Shown are the log₁₀(end-point) titers achieved following one (1°), two (2°) and three (3°) immunizations with each conjugate, each with two rabbits (a and b). Pre-immune serum samples showed no significant reactivity with the corrsponding immunogen. For example, a log₁₀(end point) titer of 5.00 corresponds to a titer of 100'000.
[a] +FA(FIA), with Freund's complete adjuvant (primary) and Freund's incomplete adjuvant (boosts)
[b] Endpoint titers of the primary (1°), first booster (2°) and second booster (3°) immunizations were defined as the last reciprocal dilution for which the UV absorbance was higher than two times the value corresponding to the pre-immune serum.

As seen from Table 1, all conjugates induced high antibody levels after the second booster immunization. A response was already detectable in most primary antisera (titers ranging from 1:100 to 1:15,000) and the steepest rise in antibody titers was observed after the second immunization, whereas a smaller increase was seen from the second to the third immunizations. It was also apparent, that the antibody titers attained without the use of adjuvants were as high, or higher, than those achieved with the use of Freund's adjuvant. This shows that good immune responses can be achieved without the use of an adjuvant.

The specificity of each hapten specific immune response was also analyzed by ELISA (Table 2). Here the ability of antibodies elicited by each conjugate to cross-react with the same antigen attached to a different LBB was measured. The results showed that a significant portion of the immune response was directed towards the antigen attached to each LBB.

TABLE 2

Specificity of the hapten specific immune responses.

| | | | Endpoint titers (log₁₀) [b] | | |
|---|---|---|---|---|---|
| Immunogen [a] | Rabbit | Antigen | 1° | 2° | 3° |
| LBB6-12 + FA(FIA) | 1a | LBB7-12 | 3.20 | 4.71 | 4.71 |
| LBB6-12 + FA(FIA) | 1b | LBB7-12 | <1.70 | 5.11 | 5.41 |
| LBB6-12 | 2a | LBB7-12 | 3.60 | 5.11 | 5.41 |
| LBB6-12 | 2b | LBB7-12 | <1.70 | 3.81 | 4.11 |
| LBB7-12 + FA(FIA) | 5a | LBB6-12 | <1.70 | 2.30 | 2.30 |
| LBB7-12 + FA(FIA) | 5b | LBB6-12 | <1.70 | 3.51 | 3.81 |
| LBB7-12 | 6a | LBB6-12 | <1.70 | 2.30 | 4.41 |
| LBB7-12 | 6b | LBB6-12 | <1.70 | <1.70 | <1.70 |
| LBB6-LY-CH + FA(FIA) | 3a | LBB7-LY-CH | 3.20 | 4.71 | 5.01 |
| LBB6-LY-CH + FA(FIA) | 3b | LBB7-LY-CH | 2.90 | 3.81 | 4.41 |
| LBB6-LY-CH | 4a | LBB7-LY-CH | 4.51 | 5.11 | 5.41 |
| LBB6-LY-CH | 4b | LBB7-LY-CH | 4.20 | 5.71 | 5.71 |
| LBB7-LY-CH | 7a | LBB6-LY-CH | 2.90 | 5.01 | 5.01 |
| LBB7-LY-CH | 7b | LBB6-LY-CH | <1.70 | 4.71 | 5.01 |

The antibodies generated against each immunogen were tested for cross-reaction to each antigen by ELISA. Shown are the log₁₀(end-point) titers achieved following one (1°), two (2°) and three (3°) immunizations with each conjugate, each with two rabbits (a and b).
[a] FA(FIA) with Freund's complete adjuvant (primes) and Freund's incomplete adjuvant (boosts)
[b] Endpoint titers of the primary (1°), first booster (2°) and second booster (3°) immunizations were defined as the last reciprocal dilution for which absorbance value was higher than two times the value corresponding to the pre-immune serum dilution.

ELISA

ELISA microtiter-plates (Nunc Immunoplates Polysorb F96) were coated overnight with a 5 µg/ml solution of each antigen in PBS. The wells were then washed with PBS containing 0.05% Tween 20 (PBST) and blocked with PBS containing 5% skimmed milk powder for 1 h at r.t. After blocking, the wells were washed three times with PBST and incubated with serial dilutions of rabbit serum in PBS containing 0.05% Tween 20 and 0.5% skimmed milk powder (MPBST) for 2.5 h at r.t., followed by three washes with PBST. The plates were then incubated with alkaline phosphatase-conjugated mouse anti-rabbit IgG antibody (Sigma), diluted 1:20000 in MPBST for 1 h at r.t., washed again three times with PBST and incubated in the dark with a 1 mg/ml solution of p-nitrophenyl phosphate (Sigma) in substrate buffer (50 mM sodium carbonate buffer, 1 mM $MgCl_2$, pH 9.6) at r.t. The absorbance was read after an appropriate time at 405 nm using a Bio-Rad Model 3550 microplate reader.

Example 12

Lipopeptide 9

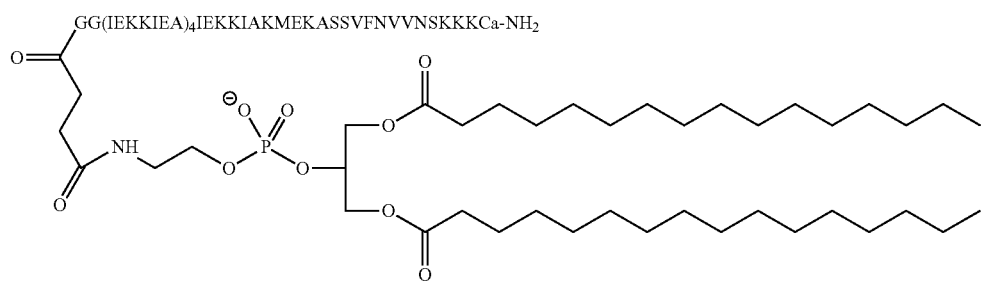

wherein the linear peptide shown corresponds to SEQ ID NO:28, wherein a D-alanine-amide denoted "a-NH$_2$" is added at the C-terminus.

This example is based on the IEKKIEA heptad repeat motif of lipopeptide 8 of Example 4, but includes in addition a correctly fused universal T-helper cell epitope [described in: Sinigaglia, F. et al., Nature, (1988), 336, 778-780] as well as extra residues at the C-terminus to improve solubility and stability, and to allow conjugation of an antigen.

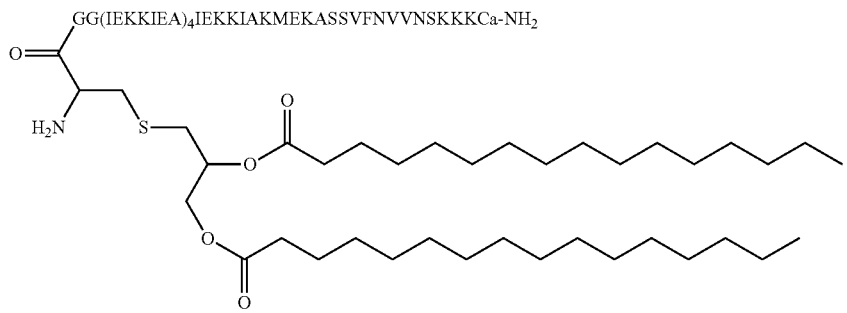

The linear peptide GGIEKKIEAIEKKIEAIEKKIEAIEK-KIEAIEKKIAKMEKASSVFNVVNSKKKCa-NH$_2$ (SEQ ID NO:28, wherein a D-alanine-amide denoted "a-NH$_2$" is added at the C-terminus) was synthesized on an Applied Biosystems ABI 433A peptide synthesizer using standard Fmoc chemistry and Rink amide MBHA resin. After loading the resin first with Fmoc-D-alanine using HBTU, HOBt, and DIEA for activation, the peptide was assembled using, in correct sequence, the following protected amino acids: Fmoc-Ala-OH, Fmoc-Asn(Trt)-OH, Fmoc-Cys(Trt)-OH, Fmoc-Glu(tBu)-OH, Fmoc-Gly-OH, Fmoc-Ile-OH, Fmoc-Lys(Boc)-OH, Fmoc-Met-OH, Fmoc-Phe-OH, Fmoc-Ser(tBu)-OH and Fmoc-Val-OH. After each coupling cycle, remaining free amino groups were acetylated using Ac$_2$O/HOBt/DIEA. After completion of the chain assembly and removal of the terminal Fmoc protecting group, the resin was washed with DMF (5×6 ml), CH$_2$Cl$_2$ (5×6 ml) and MeOH (5×6 ml) and dried in vacuo over KOH pellets. For coupling of the lipid mojety, the resin (325 mg) was swollen in CH$_2$Cl$_2$ (6 ml) for 45 min. A solution of PE-Succ-OH (120 mg, 150 µmol), PyBOP (78 mg, 150 µmol), HOBt (20 mg, 150 mmol) and DIEA (100 µl, 0.6 mmol) in CH$_2$Cl$_2$/DMF 1:2 (4.5 ml) was added. The mixture was shaken for 20 h. The resin was filtered and washed with DMF (5×6 ml), CH$_2$Cl$_2$ (5×6 ml) and MeOH (5×6 ml) and dried in vacuo over KOH pellets. For cleavage and removal of the side-chain protecting groups, the resin was treated with TFA/thioanisole/EDT/H$_2$O/TIS 75:10:10:4:1 (10 ml) with shaking for 2.5 h. The resin was filtered and the peptide was precipitated with iPr$_2$O (pre-cooled to −20°) and washed with iPr$_2$O (3×25 ml). The precipitate was allowed to air-dry overnight and the lipopeptide was purified by reverse phase HPLC on a C4 preparative column (Interchrom) using a gradient of 30 to 100% MeCN in H$_2$O (+0.1% TFA) over 28 min. Yield: 37 mg. Analytical reverse phase HPLC (Interchrom C$_4$ column, 25 to 100% MeCN in H$_2$O (+0.1% TFA) over 25 min): purity>96%, t$_R$=22.10 min. LC-MS (Zorbax C$_8$ column, 30 to 100% MeCN in H$_2$O (+0.1% HCOOH) over 10 min): t$_R$=5.32 min.; ESI-MS m/z=990.3 [M+7H]$^{7+}$; 866.6 [M+8H]$^{8+}$; 770.2 [M+9H]$^{9+}$; 693.3 [M+10H]$^{10+}$. MALDI-TOF: m/z calculated for C$_{315}$H$_{557}$N$_{74}$O$_{90}$PS$_2$: 6916.3; m/z found: 6916.8 [M+H]$^+$.

Example 13

Lipopeptide 10 wherein the linear peptide shown corresponds to SEQ ID NO:28, wherein a D-alanine-amide denoted "a-NH$_2$" is added at the C-terminus.

This example uses the same peptide sequence as Example 12, but contains a Pam$_2$-cysteine-based lipid head group (Cys ((RS)-2,3-di(palmitoyloxy)-propyl)) instead of one based on a phospholipid.

The linear peptide was synthesized on an Applied Biosystems ABI 433A peptide synthesizer using standard Fmoc chemistry and Rink amide MBHA resin, as described above for lipopeptide 9. For coupling of the lipid mojety to the N-terminus of the peptide chain, the resin (280 mg) was swollen in CH$_2$Cl$_2$ (6 ml) for 30 min. A solution of Fmoc-Cys ((RS)-2,3-di(palmitoyloxy)-propyl)-OH (134 mg, 150 µmol), PyBOP (78 mg, 150 µmol), HOBt (20 mg, 150 µmol) and DIEA (100 µl, 0.6 mmol) in CH$_2$Cl$_2$/DMF 2:1 (4.5 ml) was added. The mixture was shaken at room temperature for 20 h. The resin was filtered and washed with DMF (5×6 ml) and CH$_2$Cl$_2$ (5×6 ml). To remove the Fmoc protecting group, the resin was treated with 20% piperidine in DMF (5×4.5 ml for 2 min.). After complete removal of the Fmoc protecting group, the resin was washed with DMF (5×6 ml), CH$_2$Cl$_2$ (5×6 ml) and MeOH (5×6 ml) and dried in vacuo over KOH pellets. For cleavage and removal of the side-chain protecting groups, the resin was treated with TFA/thioanisole/EDT/H$_2$O/TIS 75:10:10:4:1 (10 ml) with shaking for 2.5 h. The lipopeptide was precipitated and purified as described for lipopeptide 9. Yield: 45 mg. Analytical reverse phase HPLC (Interchrom C$_4$ column, 25 to 100% MeCN in H$_2$O (+0.1% TFA) over 25 min.): purity>96%, t$_R$=22.71 min. LC-MS (Zorbax C$_8$ column, 30 to 100% MeCN in H$_2$O (+0.1% CHOOH) over 10 min): t$_R$=4.87 min.; ESI-MS m/z=851.1 [M+8H]$^{8+}$; 756.9 [M+9H]$^{9+}$; 681.3 [M+10H]$^{10+}$; 618.1

[M+1H]$^{11+}$. MALDI-TOF: m/z calculated for $C_{312}H_{552}N_{74}O_{85}S_3$: 6796.4; m/z found: 6798.2 [M+H]$^+$.

Example 14

Antigen bearing a gamma-maleimidobutyryl group, GMB-L21

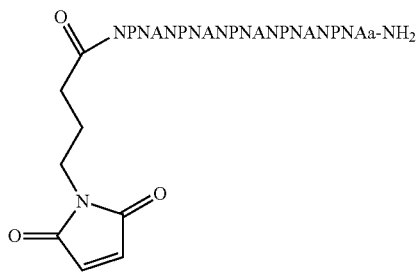

GMB-L21 wherein the linear peptide shown corresponds to SEQ ID NO:30, wherein a D-alanine-amide denoted "a-NH$_2$" is added at the C-terminus.

The peptide sequence is taken mainly from the NPNA-repeat region of the circumsporozoite (CS) protein of the malaria parasite *Plasmodium falciparum*, which has been extensively investigated for its potential as a malaria vaccine candidate [Herrington, D. A. et al., Nature, (1987), 328, 257-259]. An extra D-alanine-amide (denoted "a-NH$_2$") is added at the C-terminus to improve stability. The gamma-maleimidobutyryl (GMB) group has been added to allow conjugation with a cysteine residue in lipopeptide-9 or lipopeptide-10.

The linear peptide NPNANPNANPNANPNANPNAa-NH$_2$ (SEQ ID NO:30 with an extra D-alanine-amide added at the C-terminus) was synthesized on an Applied Biosystems ABI 433A peptide synthesizer using standard Fmoc chemistry and Rink amide MBHA resin (loading 0.69 mmol/g, 362 mg), and HBTU/HOBt/DIEA for activation. The amino acids used where Fmoc-Ala-OH, Fmoc-D-Ala-OH, Fmoc-Asn (Mtt)-OH and Fmoc-Pro-OH. After completion of the chain assembly and removal of the terminal Fmoc protecting group, the resin was washed with DMF (5×6 ml), DCM (5×6 ml) and MeOH (5×6 ml) and dried in vacuo over KOH pellets. The peptide was cleaved and the side-chain protecting groups were removed by treatment with TFA/TIS/H$_2$O 95:2.5:2.5 (10 ml) for 4 h. The peptide was precipitated in iPr$_2$O, pre-cooled to −20° and washed with iPr$_2$O (3×25 ml). The precipitate was dried in vacuo and the peptide was purified by reverse phase HPLC on a C18 preparative column (Zorbax) using a gradient of 10 to 30% MeCN in H$_2$O (+0.1% TFA) over 28 min. Yield: 162 mg. Analytical reverse phase HPLC (Interchrom C$_4$ column, 5 to 30% MeCN in H$_2$O (+0.1% TFA) over 21 min.): purity>95%, $t_R$=8.77 min. LC-MS (Zorbax C$_8$ column, 5 to 100% MeCN in H$_2$O (+0.1% CHOOH) over 10 min): $t_R$=3.61 min.; ESI-MS m/z=691.6 [M+3H]$^{3+}$. MALDI-TOF: m/z calculated for $C_{83}H_{127}N_{31}O_{32}$: 2071.1; m/z found: 2069.9 [M+H]$^+$.

To couple the GMB linker to the peptide, a solution of 4-maleimidobutyryl-N-hydroxy-succinimide ester (N-succinimidyl-4-maleimido-butyrate, 14.0 mg, 49.2 μmol, 6 equiv.) in THF (0.5 ml) was added dropwise to a stirred solution of peptide (17.0 mg, 8.2 μmol) in 5 mM NH$_4$OAc, pH 6.5 (0.5 ml). The mixture was stirred for 20 h at 4°, lyophilized and the product GMB-L21 was purified by reverse phase HPLC on a C18 preparative column (Waters) using a gradient of 10 to 40% MeCN in H$_2$O (+0.1% TFA) over 20 min. Yield: 10.4 mg. Analytical reverse phase HPLC (Zorbax C$_{18}$ column, 5 to 30% MeCN in H$_2$O (+0.1% TFA) over 25 min.: purity>95%, $t_R$=13.02 min. LC-MS (Zorbax C$_{18}$ column, 5 to 100% MeCN in H$_2$O (+0.1% CHOOH) over 10 min): $t_R$=3.15 min.; ESI-MS m/z=746.5 [M+3H]$^{3+}$ Example 15

Antigen bearing a 3-maleimido-propionyl and a polyethylene glycol spacer group, PEO8-L21

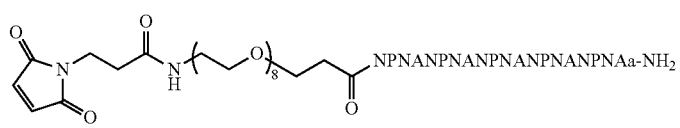

PEO8-L21 wherein the linear peptide shown corresponds to SEQ ID NO:30, wherein a D-alanine-amide denoted "a-NH$_2$" is added at the C-terminus.

The same antigen as in Example 14 based on the NPNA repeat region of the CS protein is attached to a 3-maleimido-propionyl group and a spacer group based on a polyethylene glycol [O-(2-aminoethyl)-O'-(2-carboxyethyl)-heptaethylene glycol]. The maleimido group allows conjugation with a cysteine residue in the lipopeptide building blocks.

The same linear peptide as in Example 14 was synthesized as described above. To couple the maleimido linker, a solution of the peptide (10.0 mg, 4.8 μmol) in 5 mM NH$_4$OAc, pH 6.5 (0.5 ml) was added to O-[N-(3-maleimidopropionyl)-2-aminoethyl]-O'-[3-(N-succinimidyloxy)-3-oxopropyl]-heptaethylene glycol (5.0 mg, 7.2 μmol, 1.5 equiv.) in THF (0.5 ml). Yield: 7.2 mg. Analytical reverse phase HPLC (Interchrom C$_4$ column, 5 to 30% MeCN in H$_2$O (+0.1% TFA) over 21 min.): purity>98%, $t_R$=14.27 min. LC-MS (Zorbax C$_{18}$ column, 5 to 100% MeCN in H$_2$O (+0.1% CHOOH) over 10 min): $t_R$=4.31 min.; ESI-MS m/z=882.9 [M+3H]$^{3+}$.

Example 16

Conjugate LBB9-GMB-L21

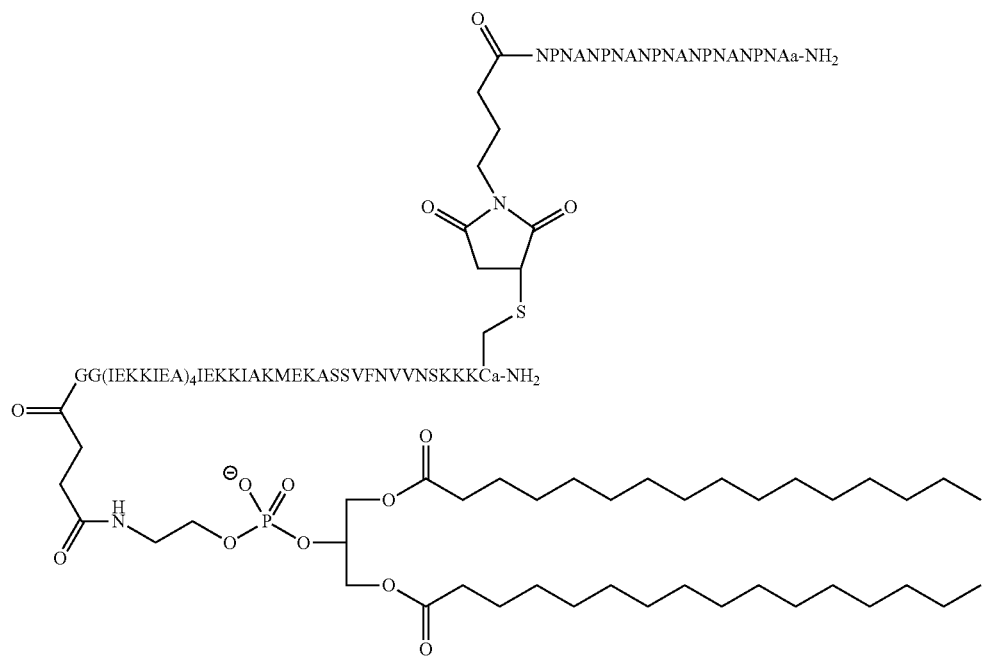

wherein the linear peptide GGIEKKIEAIEKKIEAIEK-KIEAIEKKIEAIEKKIAKMEKASSVFNVVNSKKKCa—NH$_2$ corresponds to SEQ ID NO:28 wherein a D-alanine-amide denoted "a-NH$_2$" is added at the C-terminus and wherein the linear peptide NPNANPNANPNANPNANP-NAa-NH$_2$ corresponds to SEQ ID NO:30 wherein a D-alanine-amide denoted "a-NH$_2$" is added at the C-terminus.

This example illustrates how a peptide or other epitope mimetic can be coupled to the lipopeptide building block (LBB) 9. As peptide (epitope mimetic) the molecule GMB-L21 is used, which is coupled to the Cys residue in lipopeptide 9.

To couple the peptide GMB-L21 to the lipopeptide 9, a solution of lipopeptide 9 (6.9 mg, 1.0 μmol) in H$_2$O/MeCN 1:1 (0.5 ml) was added drop-wise to a stirred solution of GMB-L21 in H$_2$O/MeCN 1:1 (1 ml, 2.7 mg, 1.2 μmol, 1.2 equiv.). The pH was adjusted carefully to pH 6.5 using 0.1 N NaOH and the mixture was stirred for 3 h. After completion of the coupling reaction, the mixture was diluted with H$_2$O containing 0.1% TFA (2 ml) and the conjugate was purified by reverse phase HPLC on a C4 semi-preparative column (Interchrom) using a gradient of 50 to 100% MeCN in H$_2$O (+0.1% TFA) over 17 min. Yield: 7.1 mg. Analytical reverse phase HPLC (Interchrom C$_4$ column, 25 to 100% MeCN in H$_2$O (+0.1% TFA) over 25 min): purity>97%, t$_R$=19.90 min. LC-MS (Zorbax C$_8$ column, 5 to 100% MeCN in H$_2$O (+0.1% CHOOH) over 10 min): t$_R$=4.83 min.; ESI-MS m/z=1310.2 [M+7H]$^{7+}$; 1145.9 [M+8H]$^{8+}$; 1019.0 [M+9H]$^{9+}$; 917.3 [M+10H]$^{10+}$; 833.8 [M+11H]$^{11+}$; 764.2 [M+12H]$^{12+}$. MALDI-TOF: m/z calculated for C$_{406}$H$_{691}$N$_{106}$O$_{125}$PS$_2$: 9152.6; m/z found: 9152.8 [M+H]$^+$.

The self-assembly properties of this lipopeptide conjugate were analyzed by dynamic light scattering (DLS), which showed that SVLPs are again formed in buffered aqueous solution. The size distribution of the particle was monomodal and highly mono-disperse, suggestive of highly ordered particles with a diameter of ca. 20 nm, which are stable under physiological conditions. The particles were also stable at higher temperatures (e.g. 37°).

Example 17

Conjugate LBB9-PEO8-L21

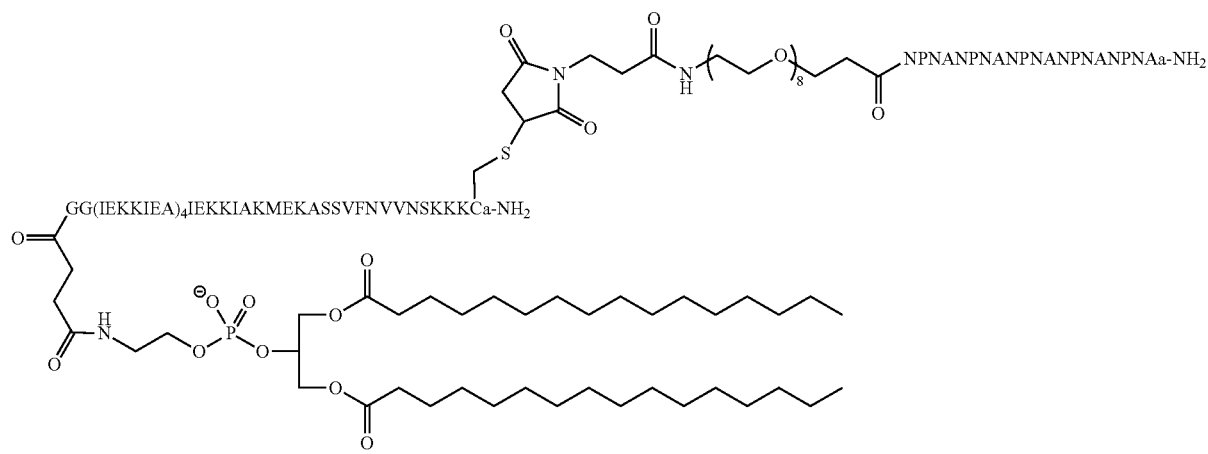

wherein the linear peptide GGIEKKIEAIEKKIEAIEK-KIEAIEKKIEAIEKKIAKMEKASSVFNVVNSKKKCa—NH$_2$ corresponds to SEQ ID NO:28, wherein a D-alanine-amide denoted "a-NH " is added at the C-terminus and wherein the linear peptide NPNANPNANPNANPNANP-NAa-NH$_2$ corresponds to SEQ ID NO:30 wherein a D-alanine-amide denoted "a-NH$_2$" is added at the C-terminus.

This example further illustrates how a peptide or other epitope mimetic can be coupled to the lipopeptide building block (LBB) 9. As peptide (epitope mimetic) the molecule PEO8-L21 is used, which is coupled to the Cys residue in lipopeptide 9.

The coupling and purification were performed as described above for LBB9-GMB-L21 using lipopeptide 9 (6.0 mg, 0.9 μmol) and PEO8-L21 (4.5 mg, 1.7 μmol, 2 equiv.). Yield: 7.2 mg. Analytical reverse phase HPLC (Interchrom C$_4$ column, 25 to 100% MeCN in H$_2$O (+0.1% TFA) over 25 min.): purity>95%, $t_R$=19.82 min. LC-MS (Zorbax C$_8$ column, 5 to 100% MeCN in H$_2$O (+0.1% CHOOH) over 10 min): $t_R$=4.93 min.; ESI-MS m/z=1366.0 [M+7H]$^{7+}$; 1196.9 [M+8H]$^{8+}$; 1064.0 [M+9H]$^{9+}$; 957.8 [M+10H]$^{10+}$. MALDI-TOF: m/z calculated for C$_{424}$H$_{727}$N$_{108}$O$_{133}$PS$_2$: 9561.1; m/z found: 9561.8 [M+H]$^+$.

The self-assembly properties of this lipopeptide conjugate were analyzed by dynamic light scattering (DLS), which showed that SVLPs are again formed in buffered aqueous solution. The size distribution of the particle was monomodal and highly monodisperse, suggestive of highly ordered particles with a diameter of ca. 24 nm, which are stable under physiological conditions. The particles were also stable at higher temperatures (e.g. 37°).

Example 18

Conjugate LBB10-GMB-L21

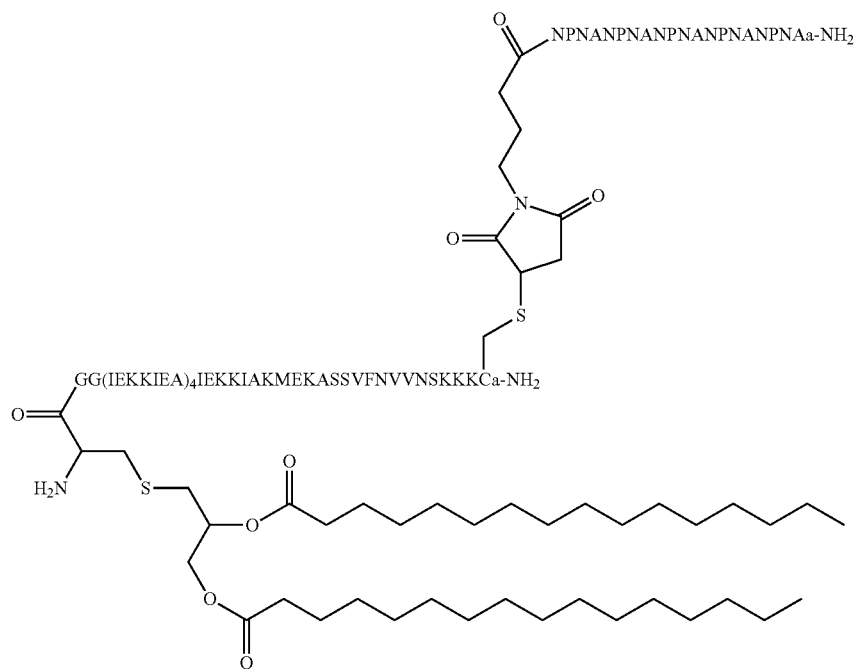

wherein the linear peptide GGIEKKIEAIEKKIEAIEK-KIEAIEKKIEAIEKKIAKMEKASSVFNVVNSKKKCa—NH$_2$ corresponds to SEQ ID NO:28, wherein a D-alanine-amide denoted "a-NH$_2$" is added at the C-terminus and wherein the linear peptide NPNANPNANPNANPNANP-NAa-NH$_2$ corresponds to SEQ ID NO:30 wherein a D-alanine-amide denoted "a-NH$_2$" is added at the C-terminus. This example illustrates how a peptide or other epitope mimetic can be coupled to the lipopeptide building block (LBB) 10. As peptide (epitope mimetic) the molecule GMB-L21 is used, which is coupled to the Cys residue in lipopeptide 10.

The coupling and purification were performed as described for LBB9-GMB-L21 using lipopeptide 10 (6.8 mg, 1.0 μmol) and GMB-L21 (2.7 mg, 1.2 μmol, 1.2 equiv.). Yield: 7.4 mg. Analytical reverse phase HPLC (Interchrom C$_4$ column, 25 to 100% MeCN in H$_2$O (+0.1% TFA) over 25 min.): purity>97%, $t_R$=19.64 min. LC-MS (Zorbax C$_8$ column, 5 to 100% MeCN in H$_2$O (+0.1% CHOOH) over 10 min): $t_R$=4.81 min.; ESI-MS m/z=1130.9 [M+8H]$^{8+}$; 1005.7 [M+9H]$^{9+}$; 905.3 [M+10H]$^{10+}$; 822.7 [M+1H]$^{11+}$; 754.4 [M+12H]$^{12+}$. MALDI-TOF: m/z calculated for C$_{403}$H$_{686}$N$_{106}$O$_{120}$S$_3$: 9032.6; m/z found: 9032.2 [M+H]$^+$.

The self-assembly properties of this lipopeptide conjugate were analyzed by dynamic light scattering (DLS), which showed that SVLPs are again formed in buffered aqueous solution. The size distribution of the particle was monomodal and highly monodisperse, suggestive of highly ordered particles with a diameter of ca. 20 nm, which are stable under physiological conditions. The particles were also stable at higher temperatures (e.g. 37°).

Example-19

Immunizations with LBB9-GMB-L21, LBB9-PEO8-L21 and LBB10-GMB-L21

This example shows that the conjugates described above are highly immunogenic upon injection into animals, and elicit strong humoral immune responses. The immunizations were carried out as described in Example 11.

Thus as before, New Zealand White rabbits (groups of two) were immunized s.c. with 150 μg lipopeptide (either LBB9-PEO8-L21 or LBB10-GMB-L21) formulated in PBS, pH 7.4 (400 μl). Immunizations were performed on days 0, 28 and 56. Bleedings were performed on days 0, 14, 38 and 66. The sera were analyzed by ELISA for IgG responses. Table-3 summarizes the end-point titres achieved. No adjuvants were used in these immunizations.

In addition, the sera from the immunized animals have been shown by immunofluorescence assays to contain a high titre (>10,000) of antibodies that bind to the CS protein on *Plasmodium falciparum* sporozoites, thus showing that a major part of the immune response to these constructs is directed to the peptide antigen containing the NPNA-repeat motifs.

TABLE 3

| Immunogenicity of conjugates | | | | |
|---|---|---|---|---|
| | | $\log_{10}$ (Endpoint titers) [b] | | |
| Conjugate used [a] | Rabbit | 1° | 2° | 3° |
| LBB9-PEO8-L21 | 1a | 3.13 | 3.82 | 4.82 |
| LBB9-PEO8-L21 | 1b | 4.44 | 5.11 | 5.05 |
| LBB10-GMB-L21 | 3a | 1.70 | 4.55 | 4.88 |
| LBB10-GMB-L21 | 3b | 3.59 | 3.76 | 4.39 |

Shown are the $\log_{10}$(end-point) titers achieved following one (1°), two (2°) and three (3°) immunizations with each conjugate, each with two rabbits (a and b). Pre-immune serum samples showed no significant reactivity with the corresponding immunogen. For example, a $\log_{10}$(end point) titer of 5.00 corresponds to a titer of 100'000.
[a] no adjuvants were used
[b] Endpoint titers of the primary (1°), first booster (2°) and second booster (3°) immunizations were defined as the last reciprocal dilution for which the UV absorbance was higher than two times the value corresponding to the pre-immune serum.

The invention claimed is:

1. A lipopeptide building block comprising a lipid moiety and a coiled-coil peptide domain comprising three to eight heptad motifs:

wherein, i) the said coiled-coil peptide domain comprises between 21 and 80 amino acid residues, ii) the said coiled-coil peptide domain is linked covalently to the lipid moiety, optionally via a linker, iii) each heptad motif is denoted by amino acid residues 'abcdefg', wherein the amino acid residues at positions 'a' and 'd' are selected from the group consisting of A, I, L, M, V, F, Y and W; and amino acid residues at positions 'b, c, e, f and g' in each heptad motif comprises no proline, and iv) the lipopeptide is optionally linked to an antigen.

2. A lipopeptide building block comprising a peptide chain comprising a coiled-coil domain, linked covalently to a lipid moiety comprising two or three long hydrocarbyl chains, and optionally linked to an antigen, wherein the peptide chain comprises a peptide of SEQ ID NO:1 to 29.

3. The lipopeptide building block according to claim 2 wherein the peptide chain comprises a peptide of SEQ ID NO:1 to 27.

4. The lipopeptide building block according to claim 2 wherein the peptide chain comprises a peptide of SEQ ID NO:1 to 4.

5. The lipopeptide building block according to claim 2 wherein the peptide chain comprises a peptide of SEQ ID NO:28.

6. The lipopeptide building block according to claim 2 wherein the peptide chain comprises a peptide of SEQ ID NO:29.

7. Lipopeptide building block according to claim 1 wherein the lipid moiety is one of types $Z^1$ to $Z^8$

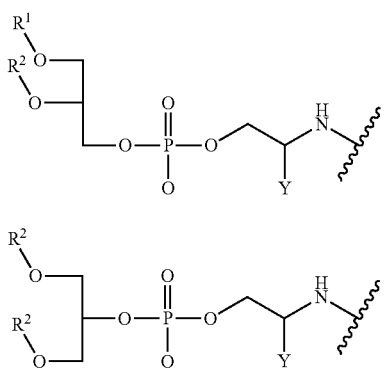

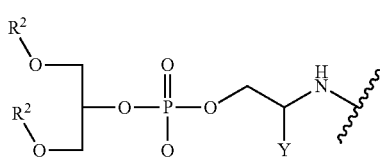

wherein $R^1$ and $R^2$ are long hydrocarbyl or long hydrocarbyl-(CO)—; and Y is H or COOH,

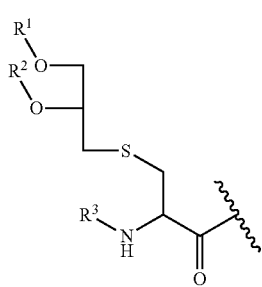

wherein $R^1$, $R^2$ and $R^3$ are long hydrocarbyl or $R^1$ and $R^2$ are long hydrocarbyl-(CO)— and $R^3$ is H or acetyl,

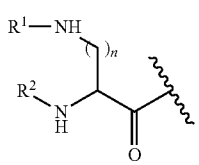

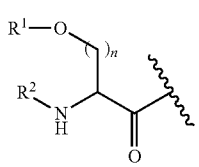

wherein $R^1$ and $R^2$ are long hydrocarbyl-(CO)— and n is 1, 2, 3 or 4, or

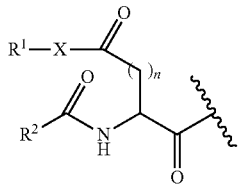

wherein $R^1$ and $R^2$ are long hydrocarbyl, X is O or NH, and n is 1, 2, 3 or 4, or

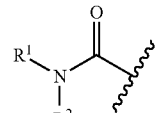

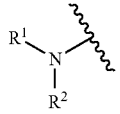

wherein $R^1$ and $R^2$ are long hydrocarbyl, and wherein long hydrocarbyl is straight or branched alkyl or alkenyl consisting of between 8 and 25 carbon atoms and optionally one, two or three double bonds in the chain.

8. The lipopeptide building block according to claim 7 wherein the lipid moiety is di-palmitoyl-S-glycerylcysteinyl of formula $Z^3$, wherein $R^1$ and $R^2$ are palmitoyl and $R^3$ is H or acetyl.

9. The lipopeptide building block according to claim 1 wherein the peptide chain PC is covalently linked to the lipid moiety LM at or near the N terminus or the C terminus.

10. The lipopeptide building block according to claim 1 wherein the peptide chain PC is covalently linked to the lipid moiety LM at or near the N terminus or the C terminus via a linker.

11. The lipopeptide building block according to claim 10 wherein the peptide chain PC is covalently linked to the lipid moiety LM at or near the N terminus via a linker as in formula (2) or (3),

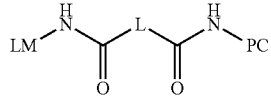

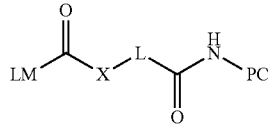

wherein L is a linker $L^1$ to $L^{10}$

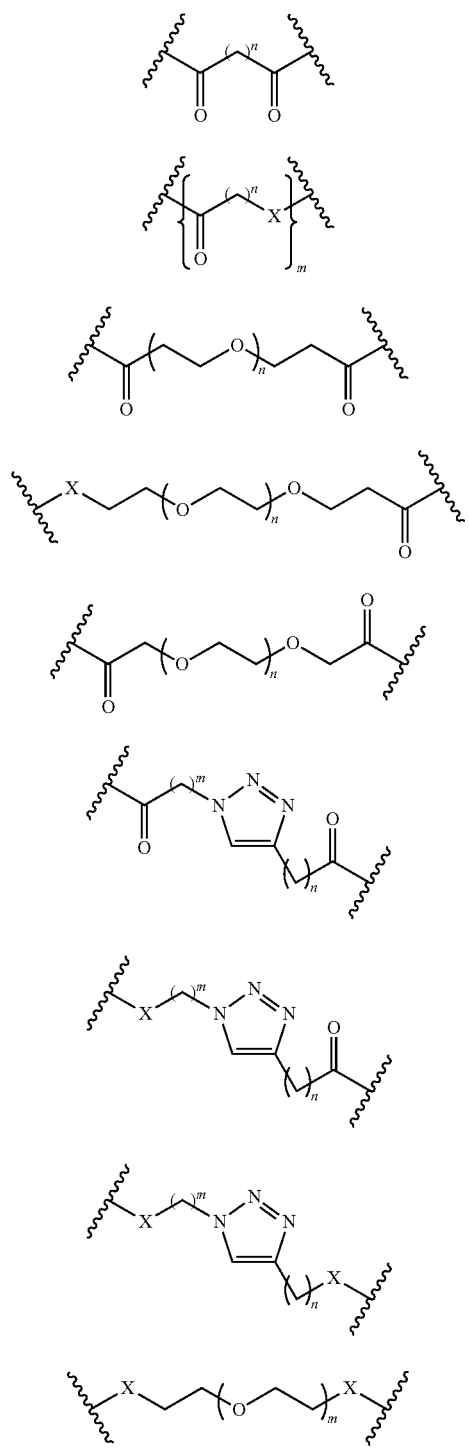

$L^1$ $L^2$ $L^3$ $L^4$ $L^5$ $L^6$ $L^7$ $L^8$ $L^9$

-continued

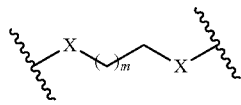

$L^{10}$ wherein X is O or NH, m is between 1 and 20 and n is between 1 and 20.

12. The lipopeptide building block according to claim 1 wherein an antigen is covalently attached at or near the other end of the peptide chain.

13. The lipopeptide building block according to claim 12 wherein the antigen is selected from a peptide, a protein, an epitope mimetic, a carbohydrate or a hapten.

14. Helical lipopeptide bundles comprising two, three, four, five, six or seven lipopeptide building blocks, wherein each of said lipopeptide building blocks comprises a lipid moiety and a coiled-coil peptide domain comprising three to eight heptad motifs:
   i) the said coiled-coil peptide domain comprises between 21 and 80 amino acid residues,
   ii) the said coiled-coil peptide domain is linked covalently to the lipid moiety, optionally via a linker,
   iii) each heptad motif is denoted by amino acid residues 'abcdefg', wherein the amino acid residues at positions 'a' and 'd' are selected from the group consisting of A, I, L, M, V, F, Y and W; and amino acid residues at positions 'b, c, e, f and g' in each heptad motif comprises no proline, and
   iv) the lipopeptide is optionally linked to an antigen.

15. Synthetic virus-like particles comprising the helical lipopeptide bundles according to claim 14.

16. A process for producing helical lipopeptide bundles comprising two, three, four, five, six or seven lipopeptide building blocks or synthetic virus-like particles comprising said helical lipopeptide bundles said process comprising:
   providing lipopeptide building blocks of claim 1, and equilibrating said building blocks in aqueous solution forming a self-assembly of said building blocks in said aqueous solution, wherein the coiled-coil domains in the lipopeptide building blocks oligomerize to form said helical lipopeptide bundles or said synthetic virus-like particles.

17. A pharmaceutical composition comprising said helical lipopeptide bundles of claims 14 carrying antigens.

18. The pharmaceutical composition according to claim 17 wherein the antigen is derived from the circumsporozoite (CS) protein of malaria parasite *Plasmodium falciparum*.

19. A pharmaceutical composition comprising a synthetic virus-like particle of claim 15 comprising said helical lipopeptide bundles carrying antigens.

20. The pharmaceutical composition according to claim 19 wherein the antigen is derived from the circumsporozoite (CS) protein of malaria parasite *Plasmodium falciparum*.

* * * * *

SEQUENCE LISTING

```
<160> NUMBER OF SEQ ID NOS: 30

<210> SEQ ID NO 1
<211> LENGTH: 52
<212> TYPE: PRT
<213> ORGANISM: Artificial sequence
<220> FEATURE:
<223> OTHER INFORMATION: derived from RSV F glycoprotein

<400> SEQUENCE: 1

Gly Gly Ala Val Ser Lys Val Leu His Leu Glu Gly Glu Val Asn Lys
1               5                   10                  15

Ile Lys Ser Ala Leu Leu Ser Thr Asn Lys Ala Val Val Ser Leu Ser
            20                  25                  30

Asn Gly Val Ser Val Leu Thr Ser Lys Val Leu Asp Leu Lys Asn Tyr
        35                  40                  45

Ile Asp Lys Gln
    50

<210> SEQ ID NO 2
<211> LENGTH: 53
<212> TYPE: PRT
<213> ORGANISM: Artificial sequence
<220> FEATURE:
<223> OTHER INFORMATION: heptad repeats and protein derived from gp41 of
      HIV-1 JR-FL

<400> SEQUENCE: 2

Ser Gly Ile Lys Lys Glu Ile Glu Ala Ile Lys Lys Glu Gln Glu Ala
1               5                   10                  15

Ile Lys Lys Lys Ile Glu Ala Ile Glu Arg Met Leu Gln Leu Thr Val
            20                  25                  30

Trp Gly Ile Lys Gln Leu Gln Ala Arg Val Leu Ala Val Glu Arg Tyr
        35                  40                  45

Leu Gly Asp Cys Gly
    50

<210> SEQ ID NO 3
<211> LENGTH: 44
<212> TYPE: PRT
<213> ORGANISM: Artificial sequence
<220> FEATURE:
<223> OTHER INFORMATION: de novo designed coiled coil

<400> SEQUENCE: 3
```

```
Gly Gly Ile Glu Lys Lys Ile Glu Ala Ile Glu Lys Lys Ile Glu Ala
1               5                   10                  15

Ile Glu Lys Lys Ile Glu Ala Ile Glu Lys Lys Ile Glu Ala Ile Glu
                20                  25                  30

Lys Lys Ile Glu Ala Ile Glu Lys Lys Ile Glu Cys
            35                  40
```

<210> SEQ ID NO 4
<211> LENGTH: 20
<212> TYPE: PRT
<213> ORGANISM: Artificial sequence
<220> FEATURE:
<223> OTHER INFORMATION: derived from V3-loop of the HIV-1 gp120
      glycoprotein

<400> SEQUENCE: 4

```
Asn Cys Arg Lys Ser Ile His Ile Gly Pro Gly Arg Ala Phe Tyr Thr
1               5                   10                  15

Thr Gly Cys Gly
            20
```

<210> SEQ ID NO 5
<211> LENGTH: 52
<212> TYPE: PRT
<213> ORGANISM: Influenza virus

<400> SEQUENCE: 5

```
Gly Ser Thr Gln Ala Ala Ile Asp Gln Ile Asn Gly Lys Leu Asn Arg
1               5                   10                  15

Val Ile Glu Lys Thr Asn Glu Lys Phe His Gln Ile Glu Lys Glu Phe
                20                  25                  30

Ser Glu Val Glu Gly Arg Ile Gln Asp Leu Glu Lys Tyr Val Glu Asp
            35                  40                  45

Thr Lys Cys Gly
    50
```

<210> SEQ ID NO 6
<211> LENGTH: 46
<212> TYPE: PRT
<213> ORGANISM: Human immunodeficiency virus

<400> SEQUENCE: 6

```
Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
                20                  25                  30

Ala Arg Ile Leu Ala Val Glu Arg Tyr Leu Gly Asp Cys Gly
            35                  40                  45
```

<210> SEQ ID NO 7
<211> LENGTH: 56
<212> TYPE: PRT
<213> ORGANISM: Bovine immunodeficiency virus

<400> SEQUENCE: 7

```
Gly Gly Glu Arg Val Val Gln Asn Val Ser Tyr Ile Ala Gln Thr Gln
1               5                   10                  15

Asp Gln Phe Thr His Leu Phe Arg Asn Ile Asn Asn Arg Leu Asn Val
                20                  25                  30

Leu His His Arg Val Ser Tyr Leu Glu Tyr Val Glu Glu Ile Arg Gln
            35                  40                  45
```

```
Lys Gln Val Phe Phe Gly Cys Gly
    50                  55

<210> SEQ ID NO 8
<211> LENGTH: 56
<212> TYPE: PRT
<213> ORGANISM: Feline immunodeficiency virus

<400> SEQUENCE: 8

Gly Gly Ala Thr His Gln Glu Thr Ile Glu Lys Val Thr Glu Ala Leu
1               5                   10                  15

Lys Ile Asn Asn Leu Arg Leu Val Thr Leu Glu His Gln Val Leu Val
            20                  25                  30

Ile Gly Leu Lys Val Glu Ala Met Glu Lys Phe Leu Tyr Thr Ala Phe
        35                  40                  45

Ala Met Gln Glu Leu Gly Cys Gly
    50                  55

<210> SEQ ID NO 9
<211> LENGTH: 56
<212> TYPE: PRT
<213> ORGANISM: Equine infectious anemia virus

<400> SEQUENCE: 9

Gly Gly Asn His Thr Phe Glu Val Glu Asn Ser Thr Leu Asn Gly Met
1               5                   10                  15

Asp Leu Ile Glu Arg Gln Ile Lys Ile Leu Tyr Ala Met Ile Leu Gln
            20                  25                  30

Thr His Ala Arg Val Gln Leu Leu Lys Glu Arg Gln Gln Val Glu Glu
        35                  40                  45

Thr Phe Asn Leu Ile Gly Cys Gly
    50                  55

<210> SEQ ID NO 10
<211> LENGTH: 58
<212> TYPE: PRT
<213> ORGANISM: Simian immunodeficiency virus

<400> SEQUENCE: 10

Gly Gly Ala Gln Ser Arg Thr Leu Leu Ala Gly Ile Val Gln Gln Gln
1               5                   10                  15

Gln Gln Leu Leu Asp Val Val Lys Arg Gln Gln Glu Leu Leu Arg Leu
            20                  25                  30

Thr Val Trp Gly Thr Lys Asn Leu Gln Thr Arg Val Thr Ala Ile Glu
        35                  40                  45

Lys Tyr Leu Lys Asp Gln Ala Gly Cys Gly
    50                  55

<210> SEQ ID NO 11
<211> LENGTH: 52
<212> TYPE: PRT
<213> ORGANISM: Caprine arthritis-encephalitis virus

<400> SEQUENCE: 11

Gly Gly Ser Tyr Thr Lys Ala Ala Val Gln Thr Leu Ala Asn Ala Thr
1               5                   10                  15

Ala Ala Gln Gln Asp Val Leu Glu Ala Thr Tyr Ala Met Val Gln His
            20                  25                  30

Val Ala Lys Gly Val Arg Ile Leu Glu Ala Arg Val Ala Arg Val Glu
        35                  40                  45
```

```
Ala Gly Cys Gly
    50

<210> SEQ ID NO 12
<211> LENGTH: 55
<212> TYPE: PRT
<213> ORGANISM: Visna virus

<400> SEQUENCE: 12

Gly Gly Ser Leu Ala Asn Ala Thr Ala Ala Gln Gln Asn Val Leu Glu
1               5                   10                  15

Ala Thr Tyr Ala Met Val Gln His Val Ala Lys Gly Ile Arg Ile Leu
            20                  25                  30

Glu Ala Arg Val Ala Arg Val Glu Ala Ile Ile Asp Arg Met Met Val
        35                  40                  45

Tyr Gln Glu Leu Asp Cys Gly
    50                  55

<210> SEQ ID NO 13
<211> LENGTH: 54
<212> TYPE: PRT
<213> ORGANISM: Human parainfluenza virus 3

<400> SEQUENCE: 13

Gly Gly Glu Ala Lys Gln Ala Arg Ser Asp Ile Glu Lys Leu Lys Glu
1               5                   10                  15

Ala Ile Arg Asp Thr Asn Lys Ala Val Gln Ser Val Gln Ser Ser Ile
            20                  25                  30

Gly Asn Leu Ile Val Ala Ile Lys Ser Val Gln Asp Tyr Val Asn Lys
        35                  40                  45

Glu Ile Val Gly Cys Gly
    50

<210> SEQ ID NO 14
<211> LENGTH: 54
<212> TYPE: PRT
<213> ORGANISM: Human parainfluenza virus 1

<400> SEQUENCE: 14

Gly Gly Glu Ala Arg Glu Ala Arg Lys Asp Ile Ala Leu Ile Lys Asp
1               5                   10                  15

Ser Ile Ile Lys Thr His Asn Ser Val Glu Leu Ile Gln Arg Gly Ile
            20                  25                  30

Gly Glu Gln Ile Ile Ala Leu Lys Thr Leu Gln Asp Phe Val Asn Asn
        35                  40                  45

Glu Ile Arg Gly Cys Gly
    50

<210> SEQ ID NO 15
<211> LENGTH: 55
<212> TYPE: PRT
<213> ORGANISM: Human parainfluenza virus 2

<400> SEQUENCE: 15

Gly Gly Lys Ala Asn Ala Asn Ala Ala Ala Ile Asn Asn Leu Ala Ser
1               5                   10                  15

Ser Ile Gln Ser Thr Asn Lys Ala Val Ser Asp Val Ile Thr Ala Ser
            20                  25                  30

Arg Thr Ile Ala Thr Ala Val Gln Ala Ile Gln Asp His Ile Asn Gly
        35                  40                  45
```

Ala Ile Val Asn Gly Cys Gly
    50                  55

<210> SEQ ID NO 16
<211> LENGTH: 54
<212> TYPE: PRT
<213> ORGANISM: Human parainfluenza virus 4a

<400> SEQUENCE: 16

Gly Gly Lys Ala Gln Glu Asn Ala Lys Leu Ile Leu Thr Leu Lys Lys
1               5                   10                  15

Ala Ala Thr Glu Thr Asn Glu Ala Val Arg Asp Leu Ala Asn Ser Asn
            20                  25                  30

Lys Ile Val Val Lys Met Ile Ser Ala Ile Gln Asn Gln Ile Asn Thr
        35                  40                  45

Ile Ile Gln Gly Cys Gly
    50

<210> SEQ ID NO 17
<211> LENGTH: 54
<212> TYPE: PRT
<213> ORGANISM: Human parainfluenza virus 4b

<400> SEQUENCE: 17

Gly Gly Lys Ala Gln Glu Asn Ala Gln Leu Ile Leu Thr Leu Lys Lys
1               5                   10                  15

Ala Ala Lys Glu Thr Asn Asp Ala Val Arg Asp Leu Thr Lys Ser Asn
            20                  25                  30

Lys Ile Val Ala Arg Met Ile Ser Ala Ile Gln Asn Gln Ile Asn Thr
        35                  40                  45

Ile Ile Gln Gly Cys Gly
    50

<210> SEQ ID NO 18
<211> LENGTH: 53
<212> TYPE: PRT
<213> ORGANISM: Measles virus

<400> SEQUENCE: 18

Gly Gly Ser Met Leu Asn Ser Gln Ala Ile Asp Asn Leu Arg Ala Ser
1               5                   10                  15

Leu Glu Thr Thr Asn Gln Ala Ile Glu Ala Ile Arg Gln Ser Gly Gln
            20                  25                  30

Glu Met Ile Leu Ala Val Gln Gly Val Gln Asp Tyr Ile Asn Asn Glu
        35                  40                  45

Leu Ile Gly Cys Gly
    50

<210> SEQ ID NO 19
<211> LENGTH: 59
<212> TYPE: PRT
<213> ORGANISM: Mumps virus

<400> SEQUENCE: 19

Gly Gly Ala Gln Thr Asn Ala Arg Ala Ile Ala Ala Met Lys Asn Ser
1               5                   10                  15

Ile Gln Ala Thr Asn Arg Ala Val Phe Glu Val Lys Glu Gly Thr Gln
            20                  25                  30

Gln Leu Ala Ile Ala Val Gln Ala Ile Gln Asp His Ile Asn Thr Ile
        35                  40                  45

-continued

```
Met Asn Thr Gln Leu Asn Asn Met Ser Cys Gly
    50                  55

<210> SEQ ID NO 20
<211> LENGTH: 55
<212> TYPE: PRT
<213> ORGANISM: Bovine respiratory syncytial virus

<400> SEQUENCE: 20

Gly Gly Ala Val Ser Lys Val Leu His Leu Glu Gly Glu Val Asn Lys
1               5                   10                  15

Ile Lys Asn Ala Leu Leu Ser Thr Asn Lys Ala Val Val Ser Leu Ser
            20                  25                  30

Asn Gly Val Ser Val Leu Thr Ser Lys Val Leu Asp Leu Lys Asn Tyr
        35                  40                  45

Ile Asp Lys Glu Gly Cys Gly
    50                  55

<210> SEQ ID NO 21
<211> LENGTH: 48
<212> TYPE: PRT
<213> ORGANISM: Ebola virus

<400> SEQUENCE: 21

Gly Gly Ala Asn Glu Thr Thr Gln Ala Leu Gln Leu Phe Leu Arg Ala
1               5                   10                  15

Thr Thr Glu Leu Arg Thr Phe Ser Ile Leu Asn Arg Lys Ala Ile Asp
            20                  25                  30

Phe Leu Leu Gln Arg Trp Gly Gly Thr Cys His Ile Leu Gly Cys Gly
        35                  40                  45

<210> SEQ ID NO 22
<211> LENGTH: 48
<212> TYPE: PRT
<213> ORGANISM: Marburg virus

<400> SEQUENCE: 22

Gly Gly Ala Asn Gln Thr Ala Lys Ser Leu Glu Leu Leu Leu Arg Val
1               5                   10                  15

Thr Thr Glu Glu Arg Thr Phe Ser Leu Ile Asn Arg His Ala Ile Asp
            20                  25                  30

Phe Leu Leu Thr Arg Trp Gly Gly Thr Cys Lys Val Leu Gly Cys Gly
        35                  40                  45

<210> SEQ ID NO 23
<211> LENGTH: 43
<212> TYPE: PRT
<213> ORGANISM: Rous sarcoma virus

<400> SEQUENCE: 23

Gly Gly Ala Asn Leu Thr Thr Ser Leu Leu Gly Asp Leu Leu Asp Asp
1               5                   10                  15

Val Thr Ser Ile Arg His Ala Val Leu Gln Asn Arg Ala Ala Ile Asp
            20                  25                  30

Phe Leu Leu Leu Ala His Gly His Gly Cys Gly
        35                  40

<210> SEQ ID NO 24
<211> LENGTH: 55
<212> TYPE: PRT
<213> ORGANISM: Staphylothermus marinus
```

-continued

```
<400> SEQUENCE: 24

Gly Ser Ile Ile Asn Glu Thr Ala Asp Asp Ile Val Tyr Arg Leu Thr
1               5                   10                  15

Val Ile Ile Asp Asp Arg Tyr Glu Ser Leu Lys Asn Leu Ile Thr Leu
            20                  25                  30

Arg Ala Asp Arg Leu Glu Met Ile Ile Asn Asp Asn Val Ser Thr Ile
        35                  40                  45

Leu Ala Ser Ile Gly Cys Gly
    50                  55

<210> SEQ ID NO 25
<211> LENGTH: 62
<212> TYPE: PRT
<213> ORGANISM: SARS coronavirus

<400> SEQUENCE: 25

Gly Gly Asn Val Leu Tyr Glu Asn Gln Lys Gln Ile Ala Asn Gln Phe
1               5                   10                  15

Asn Lys Ala Ile Ser Gln Ile Gln Glu Ser Leu Thr Thr Thr Ser Thr
            20                  25                  30

Ala Leu Gly Lys Leu Gln Asp Val Val Asn Gln Asn Ala Gln Ala Leu
        35                  40                  45

Asn Thr Leu Val Lys Gln Leu Ser Ser Asn Phe Gly Cys Gly
    50                  55                  60

<210> SEQ ID NO 26
<211> LENGTH: 67
<212> TYPE: PRT
<213> ORGANISM: Mycoplasma pneumoniae

<400> SEQUENCE: 26

Gly Gly Thr Lys Thr Glu Phe Lys Glu Phe Gln Thr Val Val Met Glu
1               5                   10                  15

Ser Phe Ala Val Gln Asn Gln Asn Ile Asp Ala Gln Gly Glu Gln Ile
            20                  25                  30

Lys Glu Leu Gln Val Glu Gln Lys Ala Gln Gly Lys Thr Leu Gln Leu
        35                  40                  45

Ile Leu Glu Ala Leu Gln Gly Ile Asn Lys Arg Leu Asp Asn Leu Glu
    50                  55                  60

Ser Cys Gly
65

<210> SEQ ID NO 27
<211> LENGTH: 38
<212> TYPE: PRT
<213> ORGANISM: Artificial sequence
<220> FEATURE:
<223> OTHER INFORMATION: heptameric coiled coil

<400> SEQUENCE: 27

Gly Gly Lys Val Lys Gln Leu Ala Asp Ala Val Glu Glu Leu Ala Ser
1               5                   10                  15
```

```
Ala Asn Tyr His Leu Ala Asn Ala Val Ala Arg Leu Ala Lys Ala Val
                20                  25                  30

Gly Glu Arg Gly Cys Gly
        35

<210> SEQ ID NO 28
<211> LENGTH: 54
<212> TYPE: PRT
<213> ORGANISM: Artificial sequence
<220> FEATURE:
<223> OTHER INFORMATION: trimeric coiled coil

<400> SEQUENCE: 28

Gly Gly Ile Glu Lys Lys Ile Glu Ala Ile Glu Lys Lys Ile Glu Ala
1               5                   10                  15

Ile Glu Lys Lys Ile Glu Ala Ile Glu Lys Lys Ile Glu Ala Ile Glu
                20                  25                  30

Lys Lys Ile Ala Lys Met Glu Lys Ala Ser Ser Val Phe Asn Val Val
                35                  40                  45

Asn Ser Lys Lys Lys Cys
    50

<210> SEQ ID NO 29
<211> LENGTH: 46
<212> TYPE: PRT
<213> ORGANISM: Artificial sequence
<220> FEATURE:
<223> OTHER INFORMATION: tetrameric coiled coil

<400> SEQUENCE: 29

Lys Leu Lys Gln Ile Glu Asp Lys Leu Glu Glu Ile Leu Ser Lys Leu
1               5                   10                  15

Tyr His Ile Glu Asn Glu Leu Ala Lys Ile Glu Lys Lys Leu Ala Lys
                20                  25                  30

Met Glu Lys Ala Ser Ser Val Phe Asn Val Val Lys Lys Cys
                35                  40                  45

<210> SEQ ID NO 30
<211> LENGTH: 20
<212> TYPE: PRT
<213> ORGANISM: Plasmodium falciparum

<400> SEQUENCE: 30

Asn Pro Asn Ala Asn Pro Asn Ala Asn Pro Asn Ala Asn Pro Asn Ala
1               5                   10                  15

Asn Pro Asn Ala
        20
```